(12) United States Patent
Sharifi-Mehr et al.

(10) Patent No.: US 12,150,653 B2
(45) Date of Patent: Nov. 26, 2024

(54) INCISION TOOLS AND METHODS OF USE

(71) Applicant: K2M, Inc., Leesburg, VA (US)

(72) Inventors: Amir Ali Sharifi-Mehr, Bloomingdale, NJ (US); Oliver Buchert, Franklin Lakes, NJ (US); Christopher P. Bell, New York, NY (US); Shawn D. Stad, Lakeville, MA (US); Alvin Sarendranath, Hackensack, NJ (US); Kornelis Poelstra, Las Vegas, NV (US)

(73) Assignee: K2M, Inc., Leesburg, VA (US)

( * ) Notice: Subject to any disclaimer, the term of this patent is extended or adjusted under 35 U.S.C. 154(b) by 692 days.

(21) Appl. No.: 17/091,739

(22) Filed: Nov. 6, 2020

(65) Prior Publication Data

US 2021/0137535 A1 May 13, 2021

Related U.S. Application Data

(60) Provisional application No. 62/931,939, filed on Nov. 7, 2019.

(51) Int. Cl.
*A61B 17/16* (2006.01)
*A61B 17/3209* (2006.01)
*A61B 34/30* (2016.01)
*A61B 17/00* (2006.01)

(52) U.S. Cl.
CPC .......... *A61B 17/16* (2013.01); *A61B 17/3209* (2013.01); *A61B 34/30* (2016.02); *A61B 2017/00477* (2013.01); *A61B 17/1671* (2013.01)

(58) Field of Classification Search
CPC .......... A61B 34/30; A61B 2017/00477; A61B 17/16; A61B 17/3209
See application file for complete search history.

(56) References Cited

U.S. PATENT DOCUMENTS

| D225,998 S | 1/1973 | Vannes Boone |
|---|---|---|
| D294,734 S | 3/1988 | Detsch |
| D294,861 S | 3/1988 | Detsch |
| D332,309 S | 1/1993 | Detsch |

(Continued)

FOREIGN PATENT DOCUMENTS

| DE | 102016101915 A1 | 8/2017 |
|---|---|---|
| EP | 1738700 A1 | 1/2007 |

OTHER PUBLICATIONS

DeWit Perennial Planter. Amazon. Oldest review date: Mar. 16, 2014. Date retrieved: Sep. 1, 2021. Retrieved from Internet: https://www.amazon.com/Tierra-Garden-F20-Perennial-Planter/dp/B0001LEMA2 (Year: 2014).

(Continued)

*Primary Examiner* — Sameh R Boles
(74) *Attorney, Agent, or Firm* — Howard & Howard Attorneys PLLC

(57) ABSTRACT

A tool for creating an incision at a surgical site includes a body for use with a robotic end effector having a proximal end and a distal end, and a blade positioned at the distal end of the body, the blade having a proximal end and a distal end, the blade having a cutting edge defining a first portion extending outwardly from or adjacent to the proximal end to a maximum width and a second portion extending inwardly from the maximum width to a sharp distal tip.

19 Claims, 22 Drawing Sheets

(56) References Cited

U.S. PATENT DOCUMENTS

| | | | |
|---|---|---|---|
| 5,318,570 A * | 6/1994 | Hood | A61B 17/8847 |
| | | | 601/2 |
| 5,370,652 A | 12/1994 | Kellan | |
| 5,447,516 A * | 9/1995 | Gardner | A61B 17/3213 |
| | | | 30/304 |
| D405,178 S | 2/1999 | Dykes | |
| 6,270,501 B1 | 8/2001 | Freiberg et al. | |
| 6,554,840 B2 | 4/2003 | Matsutani et al. | |
| 7,846,093 B2 | 12/2010 | Gorek et al. | |
| 8,010,180 B2 | 8/2011 | Quaid et al. | |
| 9,002,426 B2 | 4/2015 | Quaid et al. | |
| 9,119,655 B2 | 9/2015 | Bowling et al. | |
| 9,566,122 B2 | 2/2017 | Bowling et al. | |
| 10,028,788 B2 | 7/2018 | Kang | |
| 10,070,928 B2 | 9/2018 | Frank et al. | |
| 10,098,704 B2 | 10/2018 | Bowling et al. | |
| 10,117,713 B2 | 11/2018 | Moctezuma de la Barrera et al. | |
| 10,166,109 B2 | 1/2019 | Ferko | |
| 10,357,257 B2 | 7/2019 | Kostrzewski | |
| 10,765,438 B2 | 9/2020 | Kostrzewski | |
| 10,945,742 B2 | 3/2021 | Kostrzewski | |
| D941,470 S | 1/2022 | Sharifi-Mehr et al. | |
| 2006/0058824 A1 | 3/2006 | Kozlowski | |
| 2014/0180290 A1 | 6/2014 | Otto et al. | |
| 2015/0119987 A1 | 4/2015 | Davignon et al. | |
| 2017/0128136 A1 | 5/2017 | Post | |
| 2018/0168750 A1 | 6/2018 | Staunton et al. | |
| 2018/0325608 A1 | 11/2018 | Kang et al. | |
| 2019/0038306 A1 | 2/2019 | Lindner et al. | |
| 2019/0231447 A1 * | 8/2019 | Ebbitt | A61B 34/10 |
| 2021/0220004 A1 * | 7/2021 | Atkins | A61B 17/3213 |
| 2021/0330502 A1 | 10/2021 | Tazawa | |

OTHER PUBLICATIONS

Extended European Search Report including Written Opinion for EP20206298.0 issued Mar. 30, 2021; 10 pages.

* cited by examiner

INCISION TOOLS AND METHODS OF USE

CROSS-REFERENCE TO RELATED APPLICATIONS

This application claims the benefit of the filing date of U.S. Provisional Patent Application No. 62/931,939 filed Nov. 7, 2019, the disclosure of which is hereby incorporated herein by reference.

BACKGROUND OF THE INVENTION

The present invention generally relates to devices for creating an opening for receiving an implant, and more particularly for creating an opening in a spine.

A technique commonly referred to as spinal fixation is employed for fusing together and/or mechanically immobilizing vertebrae of the spine. Spinal fixation may also be used to alter the alignment of adjacent vertebrae relative to one another so as to change the overall alignment of the spine. Such techniques have been used effectively to treat many degenerative conditions and, in most cases, to relive pain suffered by the patient.

In some applications, a surgeon will install implants, such as pedicle screws, into the pedicles of adjacent vertebrae (along one or multiple levels of the spine) and thereafter connect the screws with a spinal rod in order to immobilize and stabilize the vertebral column. Whether conducted in conjunction with interbody fusion or across single or multiple levels of the spine, the use of pedicle screws connected by fixation rods is an important treatment method employed by surgeons.

Prior to implantation of the implant, a surgeon or other medical professional must first make an incision through the soft tissue to access the pedicle screw implant location. This access allows for the cutting tool, e.g. drill or burr, to access the bone where the hole will be drilled. However, the cutting tool may be deflected away from the desired trajectory by cantilever forces from the soft tissue. This may contribute to inaccurate and/or inefficient placement of the implant.

There remains room for improvement in the design and use of incision tools particularly for surgical efficiency while maintaining safety and accuracy during implant insertion.

SUMMARY OF THE INVENTION

The present disclosure includes an system for surgery which provides accurate and efficient placement of an implant during surgery, such as spinal surgery. In some instances, the system includes an insertion tool may be used in spinal surgery in order to make an incision through the soft tissue to allow for access to the pedicle bone. The system allows for trajectory alignment of the incision and the subsequent drilling tool and also may allow for rotational alignment so that the orientation of the incision is controlled, as desired.

According to a first aspect of the present disclosure, a tool for creating an incision at a surgical site includes a body for use with a robotic end effector having a proximal end and a distal end, and a blade positioned at the distal end of the body, the blade having a proximal end and a distal end, the blade having a cutting edge defining a first portion extending outwardly from or adjacent to the proximal end to a maximum width and a second portion extending inwardly from the maximum width to a sharp distal tip.

In other embodiments, the first portion may be convex. The second portion may be convex. The second portion may have a first side having a convex curve and a second side may have a concave curve. The blade may be detachable from the body. The distal end of the body may include an elongated projection and the blade includes a corresponding elongated recess for receiving the elongated projection of the body to attach the blade to the body. The blade may have a longitudinal axis extending along a direction from the proximal end to the distal end and the cutting portion of the blade is symmetric about the longitudinal axis. The blade may have a longitudinal axis extending along a direction from the proximal end to the distal end and the cutting portion of the blade is asymmetric about the longitudinal axis. The proximal portion of the body may have a C-shaped cross-section. A proximal portion of the body may have an attachment assembly to detachably secure the tool to the end effector. The attachment assembly may be a clip assembly including a spring-loaded leaf. The clip assembly may include a base having a first flange and the leaf has a second flange. An opening may be defined between the base and the leaf, wherein the clip assembly is moveable between a closed configuration and an open configuration and the opening is larger in the open configuration than in the closed configuration. The tool may be a first tool and in the closed configuration, a second tool is positionable within the first tool and the first tool is operatively secured to the end effector. The attachment assembly may be a hinged assembly including a hinged leaf. The tool may be part of a system that includes the tool and a guide tube attachable to a robotic arm, the tool may be configured to be positioned within the guide tube.

According to a second aspect of the present disclosure, a system for incising an opening in a patient includes a first tool having a first longitudinal axis and engageable with a robotic end effector, an incision tool having a body defining a channel for receiving the first tool and a distal portion, and a blade attached to the distal portion of the body of the incision tool, a first central axis defined by the channel of the incision tool is co-axial with a second central axis defined by the blade.

In other embodiments, a proximal portion of the body of the incision tool may have a C-shaped cross-section. The incision tool may be configured to translate relative to the first tool along the first central axis. The blade may have a proximal end and a distal end, the blade having a cutting edge defining a first portion extending outwardly from or adjacent to the proximal end to a maximum width and a second portion extending inwardly from the maximum width to a sharp distal tip. The incision tool may include a finger ring for holding the incision tool. The incision tool may be configured to clip onto the first tool to attach the incision tool to the first tool. The body may include a proximal portion at least partially surrounding the channel, the proximal portion sized and configured to fit around an outer diameter of the first tool. The body of the incision tool may include a hinged attachment member having a closed configuration in which the hinged attachment member presses on the first tool to secure the incision tool to the first tool. The first tool may be a drill bit, screwdriver, or burr. The system may include an implant configured to be attached to a distal end of the first tool.

According to another aspect of the present disclosure, a method of incising an opening in a subject includes the steps of attaching an incision tool to a first tool so that a proximal portion of the incision tool at least partially surrounds a portion of the first tool, the incision tool having a blade attached to a distal end thereof, a central axis of the blade being co-axial with a longitudinal axis of the first tool;

driving the incision tool along the first tool to cut tissue with the blade to incise an opening for inserting an implant; and retracting the blade out of the opening.

In other embodiments, the method may include the step of driving the first tool into the opening to form a bore for receiving an implant. The driving step may include translating the incision tool distally along an outer surface of the first tool. The method may include the step of attaching the blade to a distal end of the incision tool. The method may include the step of moving an attachment assembly of the incision tool to a closed configuration in which a leaf of the hinged assembly applies a force on the first tool to secure the incision tool to the incision tool. The method may include the step of moving the attachment assembly of the incision tool to an open configuration in which the incision tool is detached from the first tool. The first tool may be a screwdriver and an implant may be attached to a distal end of the screwdriver. The method may include the step of driving the implant into bone.

According to yet another aspect of the present disclosure, a method of incising an opening in a subject includes the steps of positioning a first portion of an incision tool within a robotic end effector, and advancing the incision tool distally so that a blade attached to a distal end of the incision tool cuts into tissue along a first trajectory. The method may include the step of removing the incision tool from the robotic end effector. The method may include the steps of positioning a cutting tool within the robotic end effector and advancing the cutting tool into bone along the first trajectory. The cutting tool may be a drill bit. The end effector may include a guide tube configured to receive the incision tool.

DETAILED DESCRIPTION

Figure 1:
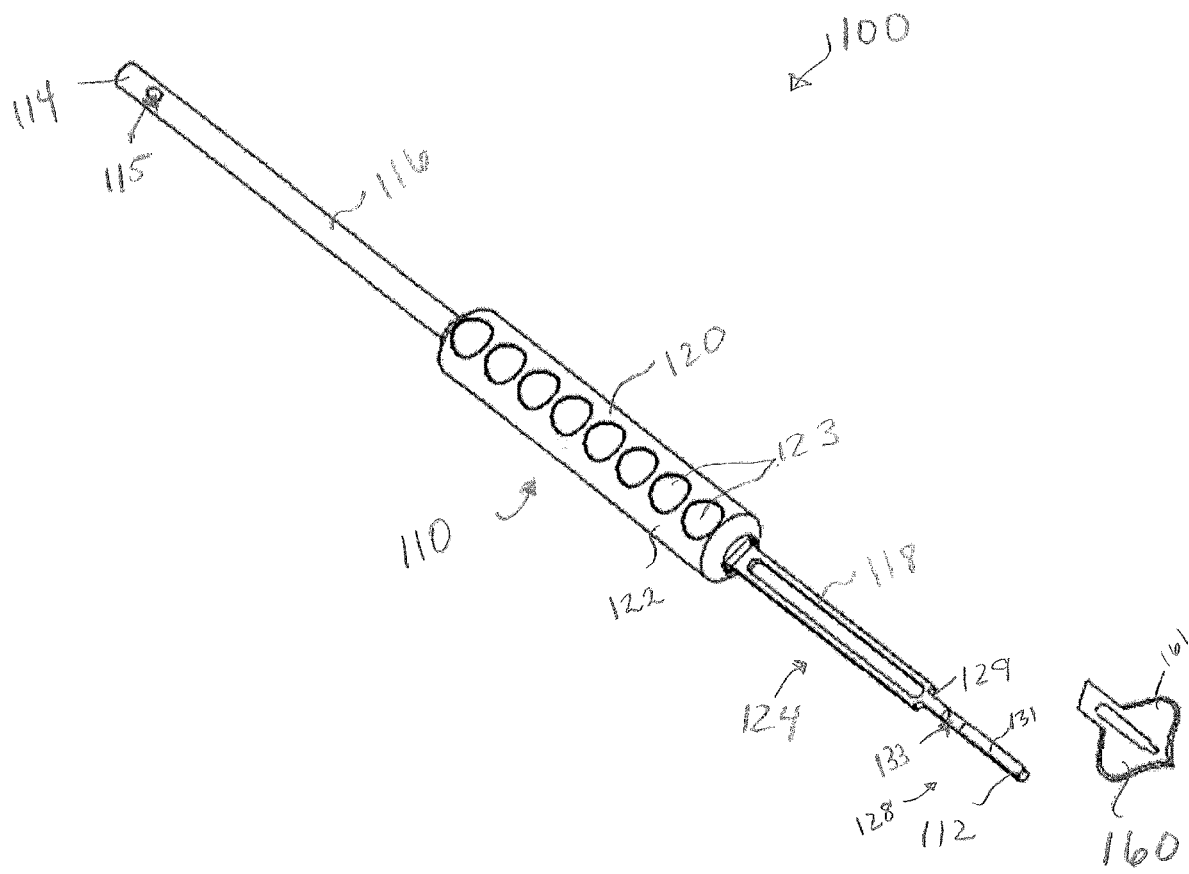
FIG. 1 is a perspective side view of an incision system including an incision tool in conjunction with a blade in accordance with a first embodiment of the present disclosure.

The present invention generally relates to incision tools and blades able to be used in conjunction with such incision tools for incision of a subject along an accurate trajectory, particularly during spinal surgery. Those of skill in the art will recognize that the following description is merely illustrative of the principles of the invention, which may be applied in various ways to provide many different alternative embodiments.

In describing certain aspects of the present inventions, specific terminology will be used for the sake of clarity. However, the inventions are not intended to be limited to any specific terms used herein, and it is to be understood that each specific term includes all technical equivalents, which operate in a similar manner to accomplish a similar purpose. In the drawings and in the description which follows, the term "proximal" refers to the end of the fixation members and instrumentation, or portion thereof, which is closest to the operator in use, while the term "distal" refers to the end of the fixation members and instrumentation, or portion thereof, which is farthest from the operator in use.

Figure 2:
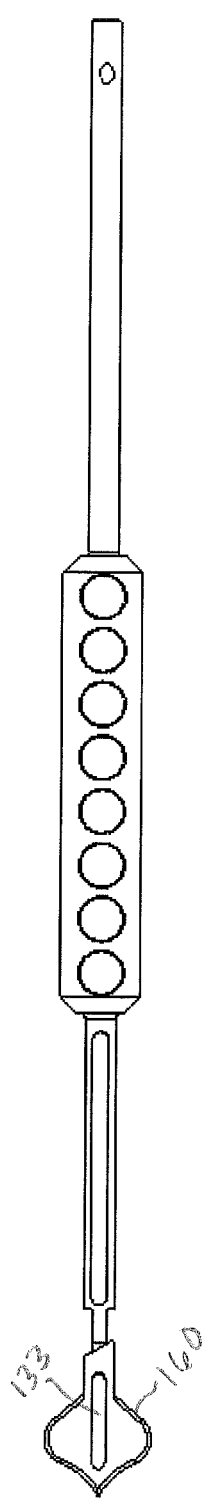
FIGS. 2 and 3 are front and side views, respectively, of the incision tool and blade of FIG. 1.
Figure 3:
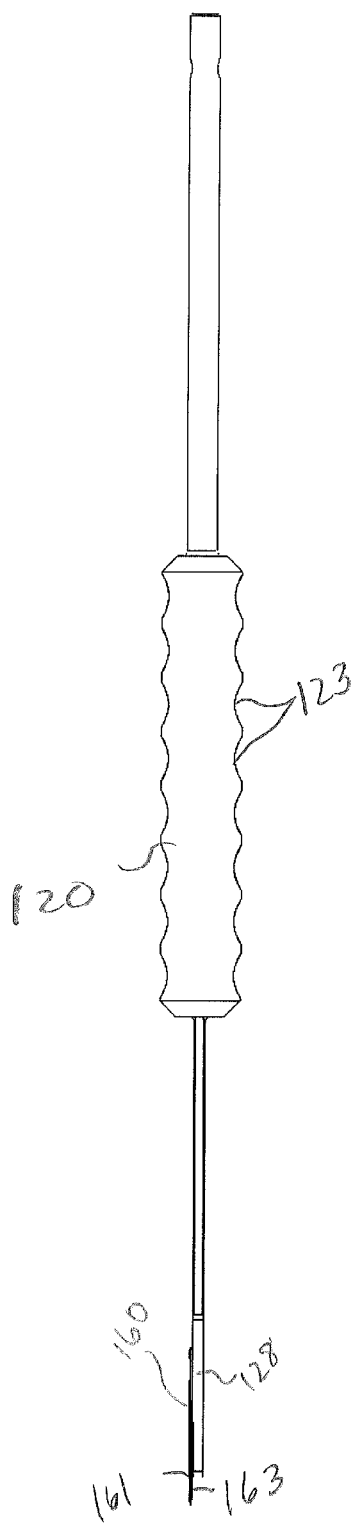

The various embodiments of the tools described below are designed to facilitate efficient and accurate implant insertion during surgery. FIGS. 1-3 depict a first embodiment of an incision system 100 including an incision tool 110 and a blade 160. Blade 160 is designed to removably attach to distal end 112 of incision tool 110.

Incision tool 110 extends along a longitudinal axis from distal end 112 to proximal end 114 and includes proximal shaft 116 and distal shaft 118. Controlling diameter 120 connects proximal shaft 116 to distal shaft 118. In the illustrated embodiment, proximal shaft 116 has a circular cross-sectional shape while distal shaft 118 has a non-circular cross-sectional shape. Proximal shaft 116 is designed to be passed through end effector 210 to mate with controlling diameter 120 such that the end effector is capable of translating incision tool 110 along the haptic line when the incision tool is received within the robotic end effector 210, as described in further detail below. Proximal shaft 116 includes aperture 115 for receiving a corresponding protrusion feature to enable quick connecting of a modular handle 127.

Distal shaft 118 includes first portion 124 and second portion 128 which forms the distal end of incision tool 110. Second portion 128 has a relatively smaller diameter than first portion 124, such that shoulder 129 is formed at the transitional point between the first and second portions. Second portion 128 is an attachment portion that forms a quick connect feature with blade 160 such that the blade attaches to the distal end of incision tool 110. The details of the connection are described in further detail below.

Figure 27:
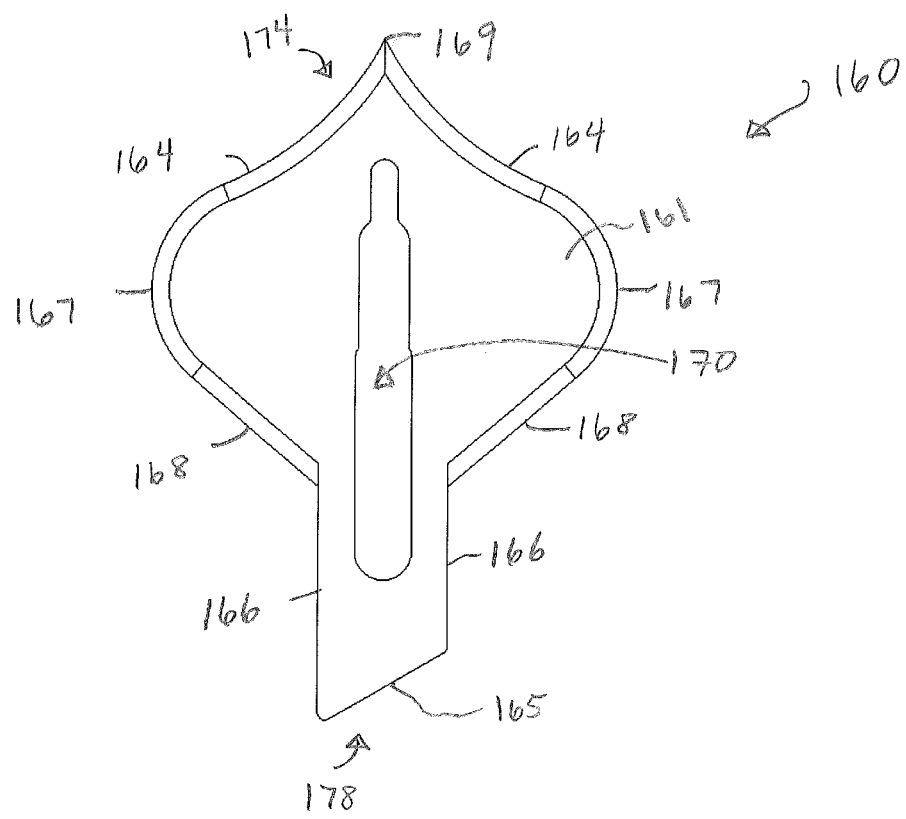
FIGS. 27-28 are a front view and a perspective side view of a blade in accordance with an embodiment of the present disclosure.

Blade 160 generally has a spade-like shape, as shown in FIGS. 1-2 and best shown in FIG. 27. Blade 160 includes distal end 174 and proximal end 178. Proximal end 178 includes terminating edge 165 connecting two lateral sides 166. Terminating edge 165 extends along a nonperpendicular angle with respect to a longitudinal axis of the blade, the longitudinal axis extending along the proximal to distal direction while sides 166 extend in a direction substantially parallel to the longitudinal axis. Although in other embodiments, sides 166 may be non-parallel to the longitudinal axis and the terminating edge 165 may be extend substantially perpendicular to the longitudinal axis. Blade 160 includes front cutting edge 164, e.g. when moving in the distal direction and/or toward the tissue, and rear cutting edge 168, e.g. when moving in the proximal direction and/or retracting from the bone. Rear cutting edge 168 extend from sides 166 and flare outward to hips 167 that define the widest diameter of the blade, defined in a direction transverse to the longitudinal axis of the blade. Hips 167 extend inward distally to define front cutting edge 164 which extends to a sharp distal tip 169. In this example, rear cutting edge 168 is convex to hips 167 and front cutting edge 164 is concave from hips 167 to distal tip 169.

Blade 160 includes substantially planar upper and lower surfaces 161, 163. Blade 160 defines elongated aperture 170 that is elongated in the direction of the longitudinal axis of the blade. Elongated aperture 170 is designed to allow a portion of distal shaft 118 of incision tool 110 to fit, by for example an interference fit, within the elongated aperture. In this regard, second portion 128 of distal shaft 118 includes raised portion 131 and a depressed portion 133, which is in the form of a channel extending across the width of second portion 128 and defined by opposing axially spaced apart inner surfaces 134.

Figure 4:
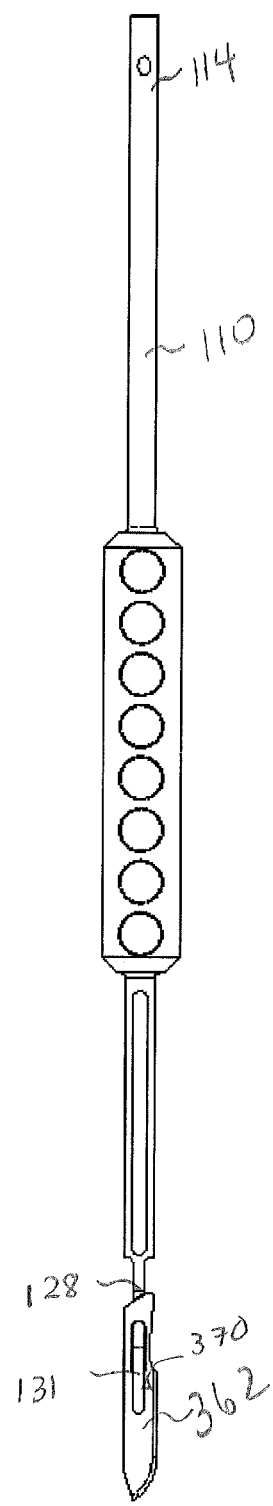
FIG. 4 is a front view of an incision system including the incision tool of FIG. 1 in conjunction with an alternative blade in accordance with an alternative embodiment of the present disclosure.

Incision tool 110 is designed to be used in conjunction with blades previously known in the art other than the novel blades disclosed herein. For example, FIG. 4 shows incision tool 110 with blade 362 connected to the second portion 128 of distal shaft 118 via a connection between elongated aperture 370 and raised portion 131. Alternative blades that may be used with the incision tools of the present disclosure are disclosed in U.S. Pat. No. 7,846,093 to Gorek et al., filed on Sep. 26, 2006, which is hereby incorporated by reference herein in its entirety.

Incision tool 110 may be used with robotic systems during spinal surgery. Robotic systems such as robotic device 200 may be used throughout the pre-operative and intra-operative stages of the surgery. Preoperative planning for surgeries may include determining the bone quality in order to optimize bone preparation. Bone quality information, such as bone density or elastic modulus, can be ascertained from preoperative scans, e.g. CT scans. The bone quality data can be used to determine optimal properties for effective implant engagement. Examples of such methods are found in U.S. Pat. No. 10,166,109 to Ferko, filed on Sep. 18, 2014, entitled "Patient Specific Bone Preparation for Consistent Effective Fixation Feature Engagement," U.S. Patent Application Publication No. 2015/0119987 to Davignon et al., filed on Oct. 28, 2014, entitled "Implant Design Using Heterogeneous Bone Properties and Probabilistic Tools to Determine Optimal Geometries for Fixation Features," and U.S. Pat. No. 10,070,928 to Frank et al., filed on Jul. 1, 2015, entitled "Implant Placement Planning," each of which is hereby incorporated by reference herein in its entirety. In addition to preoperative imaging, robotic surgery techniques may employ imaging, such as fluoroscopy, during surgery. In such cases, systems integrating the surgical system with the imaging technologies facilitate flexible and efficient intra-operative imaging. Exemplary systems are described in U.S. Pat. No. 10,028,788 to Kang, filed on Dec. 31, 2013, entitled "System for Image-Based Robotic Surgery," hereby incorporated by reference herein in its entirety.

Robotic systems and methods may be used in the performance of spine surgeries. In some such instances, robotic systems and methods may be used in the performance of spine surgeries to facilitate the insertion of implants in the patient's spine as in, for example, U.S. Patent Application Publication No. 2018/0325608 to Kang et al., filed on May 10, 2018, entitled "Robotic Spine Surgery System and Methods," the disclosure of which is hereby incorporated by reference herein in its entirety. The robotic system generally includes a manipulator and a navigation system to track a surgical tool relative to a patient's spine. The surgical tool may be manually and/or autonomously controlled. Examples of robotic systems and methods that employ both a manual and a semi-autonomous are described in U.S. Pat. No. 9,566,122 to Bowling et al., filed on Jun. 4, 2015, and entitled "Robotic System and Method for Transitioning Between Operating Modes," and U.S. Pat. No. 9,119,655 to Bowling et al., filed on Aug. 2, 2013, entitled "Surgical Manipulator Capable of Controlling a Surgical Instrument in Multiple Modes," each of which is hereby incorporated by reference herein in its entirety.

A robotic controller may be configured to control the robotic arm to provide haptic feedback to the user via the robotic arm. This haptic feedback helps to constrain or inhibit the surgeon from manually moving the incision tool beyond predefined virtual boundaries associated with the surgical procedure. Such a haptic feedback system and associated haptic objects that define the virtual boundaries are described in, for example, U.S. Pat. No. 9,002,426 to Quaid et al., filed on Jun. 23, 2008, entitled "Haptic Guidance System and Method," and U.S. Pat. No. 8,010,180 to Quaid et al., filed on Feb. 21, 2006, entitled "Systems and Methods for Haptic Control of a Surgical Tool," and U.S. Pat. No. 10,098,704 to Bowling et al., filed on May 18, 2016, entitled "System and Method for Manipulating an Anatomy," each of which is hereby incorporated by reference herein in its entirety.

In some cases of autonomous positioning, a tool center point (TCP) of a surgical tool, such as incision tools 110, 310, is brought to within a predefined distance of a starting point of a line haptic object that provides the desired trajectory. Once the tool center point is within the predefined distance of the starting point, actuation of an input causes the robotic arm to autonomously align and position the surgical tool on the desired trajectory. Once the surgical tool is in the desired position, the robotic system may effectively hold the rotational axis of the surgical tool on the desired trajectory by tracking movement of the patient and autonomously adjusting the robotic arm as needed to keep the rotational axis on the desired trajectory. Such teachings can be found in U.S. Patent Application Publication No. 2014/0180290 to Otto et al., filed on Dec. 21, 2012, entitled "Systems and Methods for Haptic Control of a Surgical Tool," which is hereby incorporated by reference herein in its entirety.

During operation of a robotic surgical system, the operation of the surgical tool can be modified based on comparing actual and commanded states of the tool relative to the surgical site is described in U.S. Patent Application Publication No. 2018/0168750 to Staunton et al., filed on Dec. 13, 2017, entitled Techniques for Modifying Tool Operation in a Surgical Robotic System Based on Comparing Actual and Commanded States of the Tool Relative to a Surgical Site," which is hereby incorporated by reference herein in its entirety. Further, robotic systems may be designed to respond to external forces applied to it during surgery, as described in U.S. Patent Application Publication No. 2017/0128136 to Post, filed on Nov. 3, 2016, entitled "Robotic System and Method for Backdriving the Same," which is hereby incorporated by reference herein in its entirety.

Further, because of the non-homogeneity of bone, applying a constant feed rate, a uniform tool path, and a constant rotational speed may not be efficient for all portions of bone. Systems and methods for controlling tools for such non-homogenous bone can be advantageous as described in U.S. Pat. No. 10,117,713 to Moctezuma de la Barrera et al., filed on Jun. 28, 2016, entitled "Robotic Systems and Methods for Controlling a Tool Removing Material From a Workpiece," which is hereby incorporated by reference herein in its entirety.

Figure 5A:
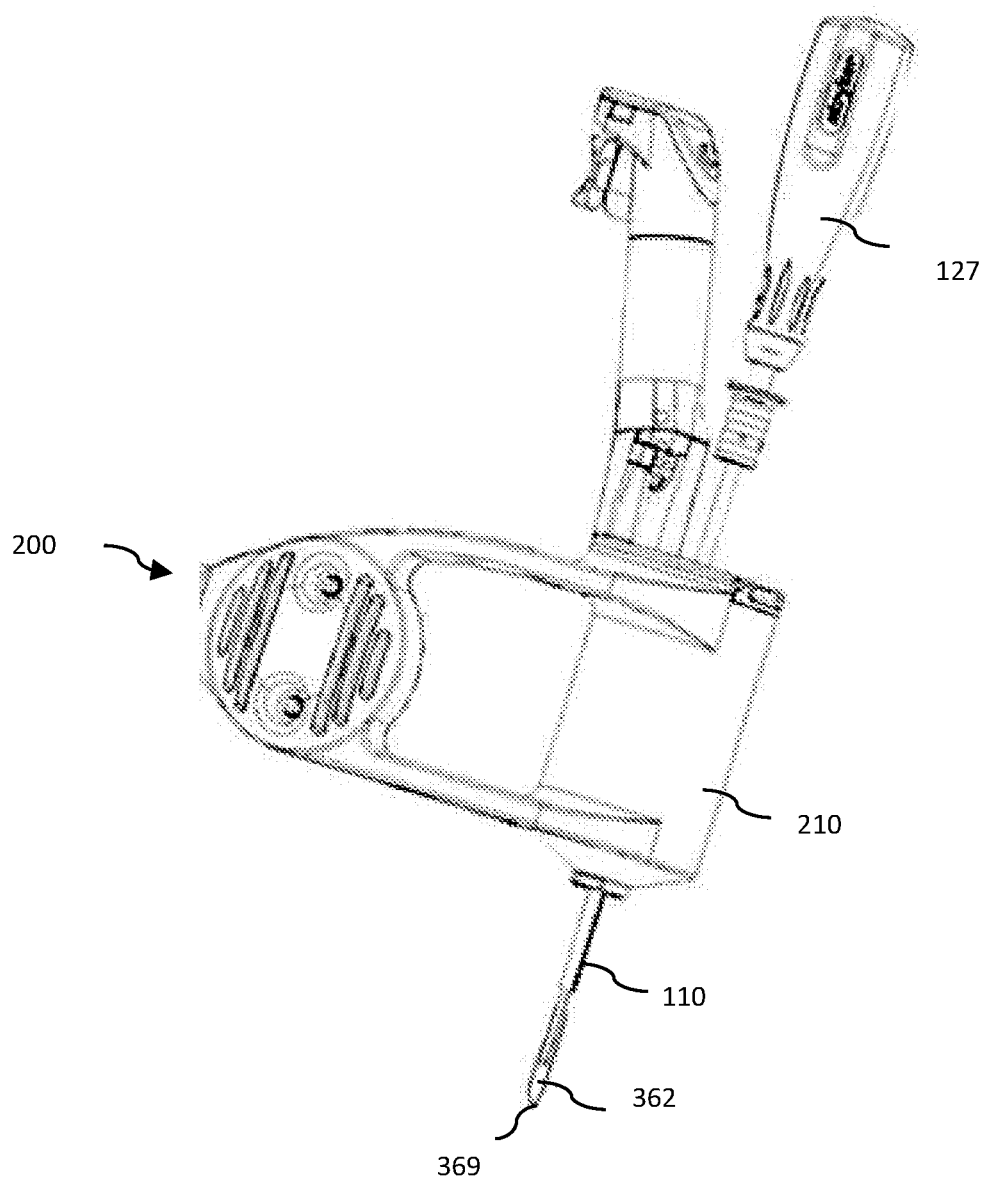
FIGS. 5A and 5B are perspective side views of the incision system of FIG. 4 in with a robot.
Figure 5B:
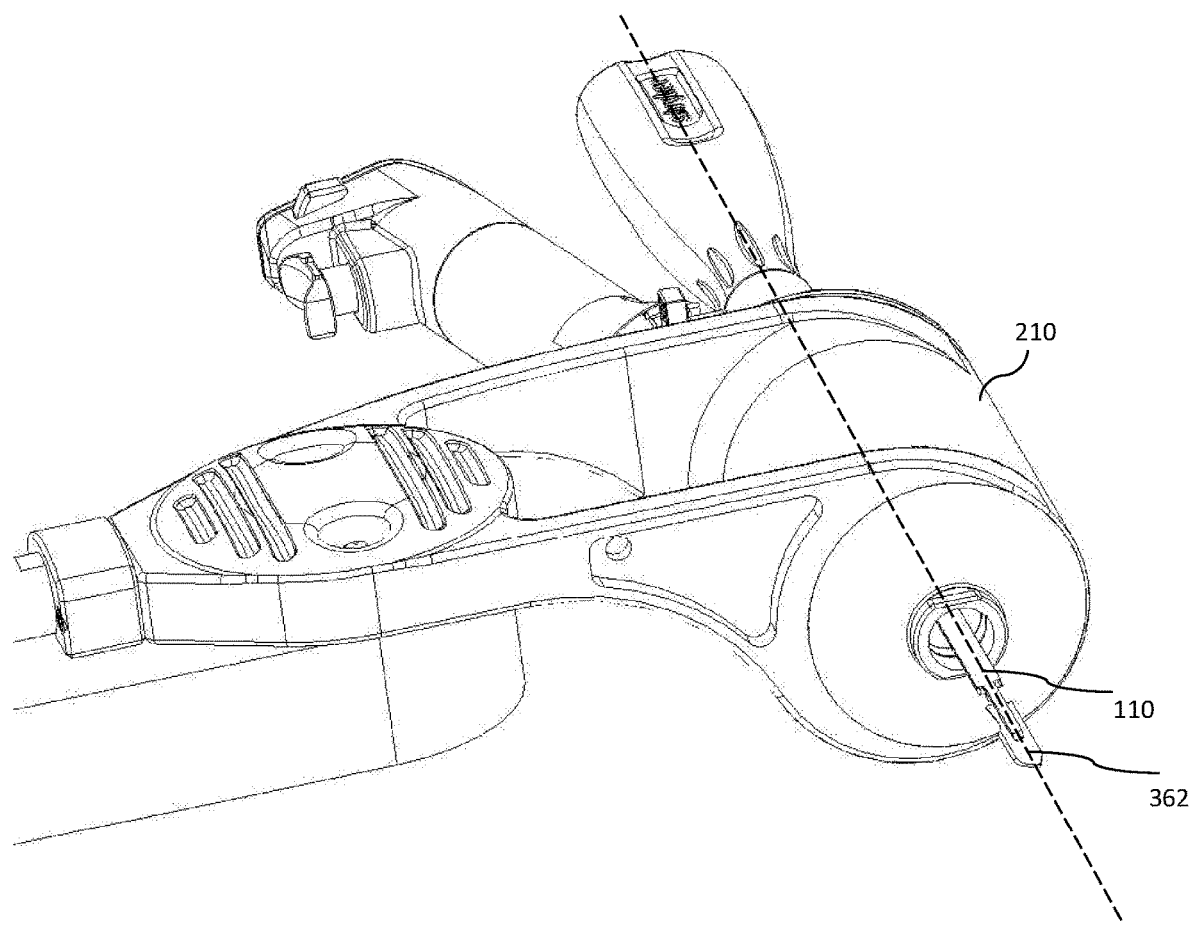
Figure 6:
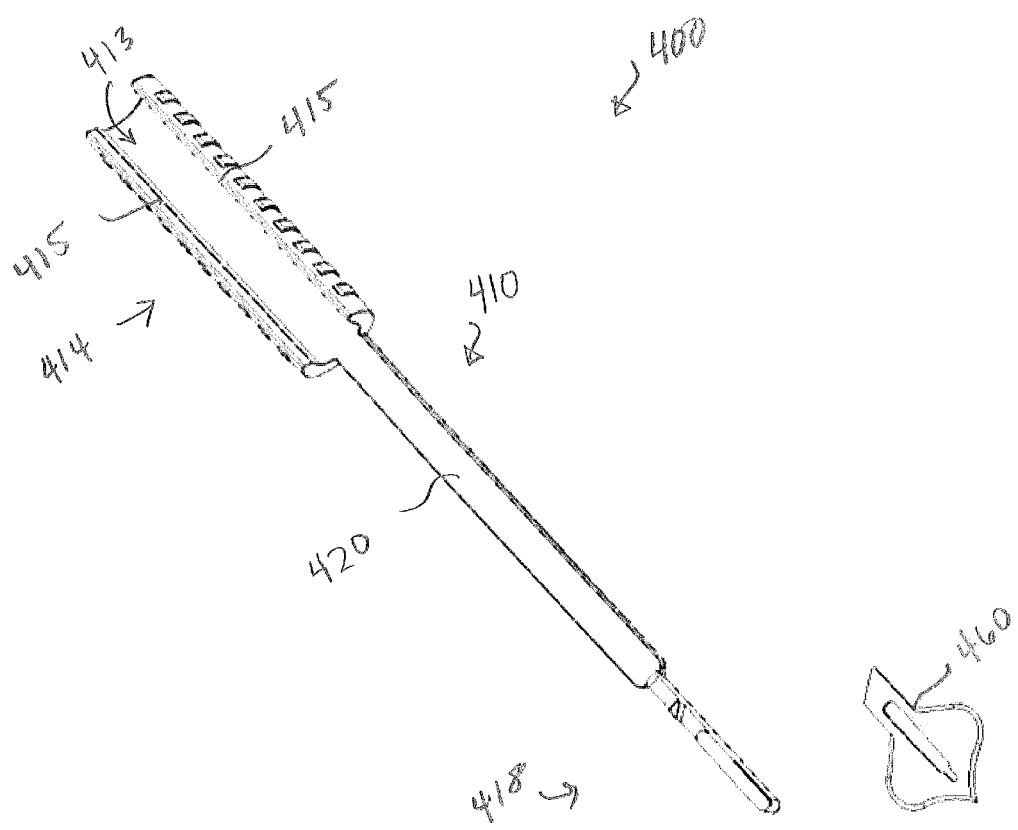
FIG. 6 is a perspective side view of an incision system including an alternative embodiment of an incision tool in conjunction with a blade in accordance with another embodiment of the present disclosure.
Figure 7:
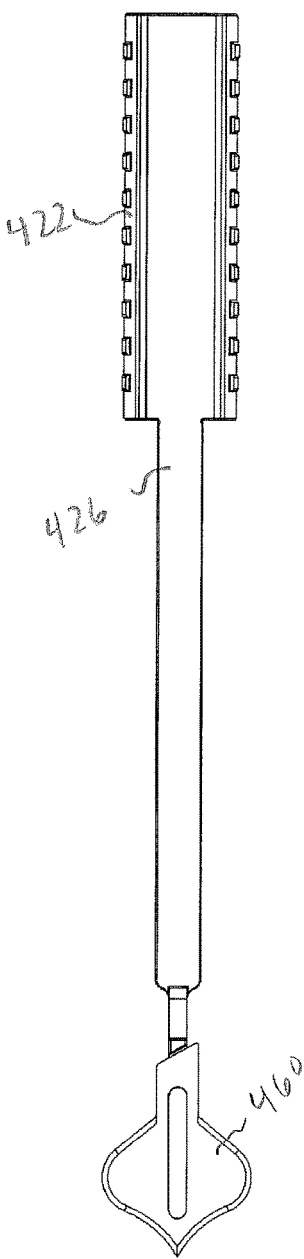
FIGS. 7, 8 and 9 are front, side and top views, respectively, of the incision system of FIG. 6.

FIGS. 5A and 5B show incision tool 110 in use with robotic device 200 including robotic end effector 210 into which proximal end 114 is positioned and attached via the attachment feature, such as the one discussed above. During use of robotic device 200 of the present disclosure, the robotic end effector 210 may be moved into a haptic control trajectory or positioned along a predetermined static trajectory. Incision tool 110 and distal tip 369 of blade 362 are coaxial with the longitudinal axis of the opening of the robotic end effector. As robotic end effector 210 is positioned near the target location, sharp distal tip 369 punctures the tissue to create the initial opening within the tissue.

When blade 160 rather than blade 362 is used with incision tool 110 and robotic end effector 210, front cutting edge 164 cuts through the tissue as the blade is advanced distally. Once the blade is advanced to meet the bone, or a desired depth within the soft tissue, the blade 160 can be retracted along the same trajectory, e.g. haptic control trajectory or predetermined static trajectory. Rear cutting edge 168 cuts any tissue that crept over the entry incision. This allows the incision and dissection to be completed in one pass along the trajectory of the robotic end effector resulting in efficiently producing an incision that is the desired width and depth as well as orientation. Further, the fewer passes that an incision tool makes, the less opportunity for skiving to occur which reduces the likelihood of an inaccurate trajectory. Additionally, the coaxial nature of the incision and the robot guided trajectory creates a soft tissue envelop that is coaxial to the planned screw trajectory which reduces the soft tissue forces and reduces the potential for skiving.

Further, robotic end effector 210 can be advanced to a position which is a fixed distance from the soft tissue surface. This helps to assess the tissue depth, maintain tactile feedback, and reduce the likelihood of inadvertent advancement of the robotic end effector while sliding the incision tools of the present disclosure along an instrument.

FIGS. 6-10 show incision system 400 which includes incision tool 410 and blade 460, identical to blade 160. Incision tool 410 includes many similar features as incision tool 110, with similar features sharing the same reference numeral, although represented in the 400 series.

Figure 11:
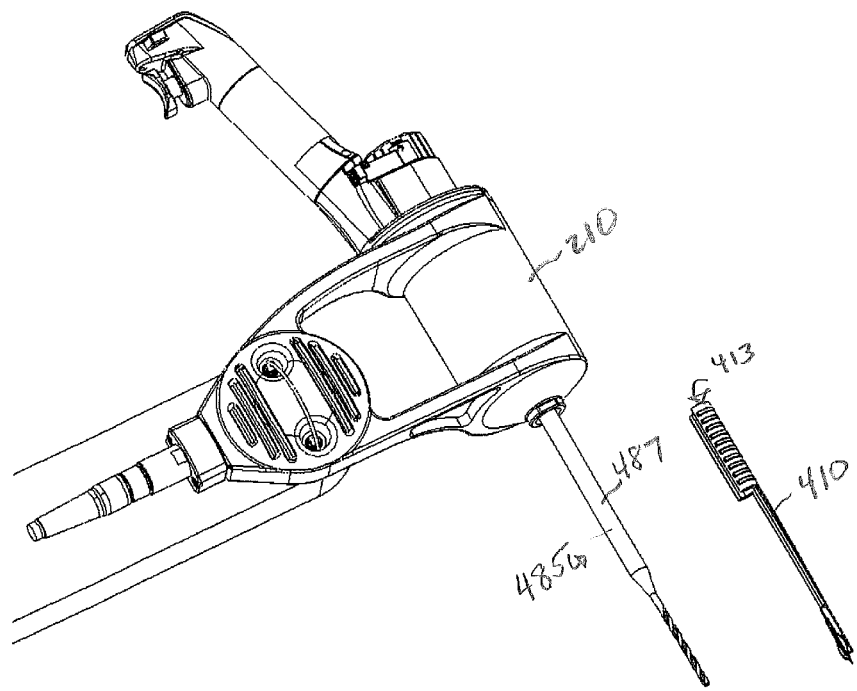
FIGS. 11-13 are perspective side views of the incision system of FIG. 6 in conjunction with a cutting tool and a robot.
Figure 12:
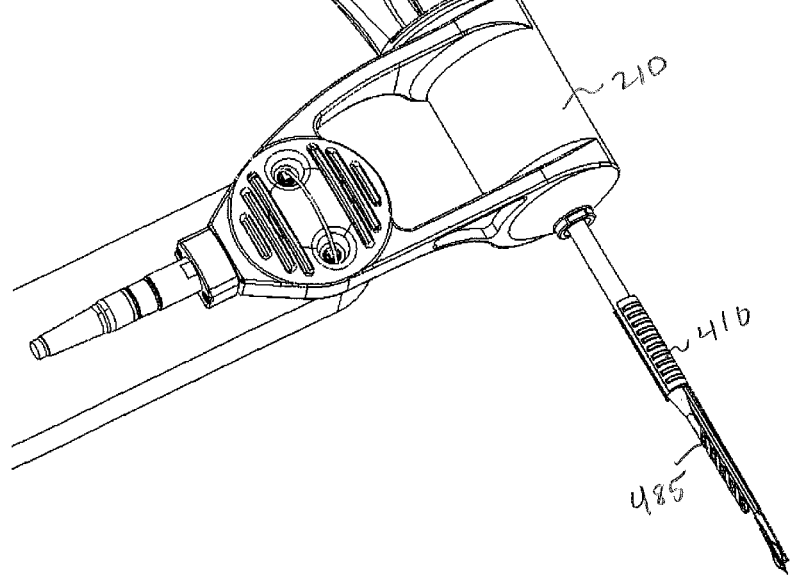
Figure 13:
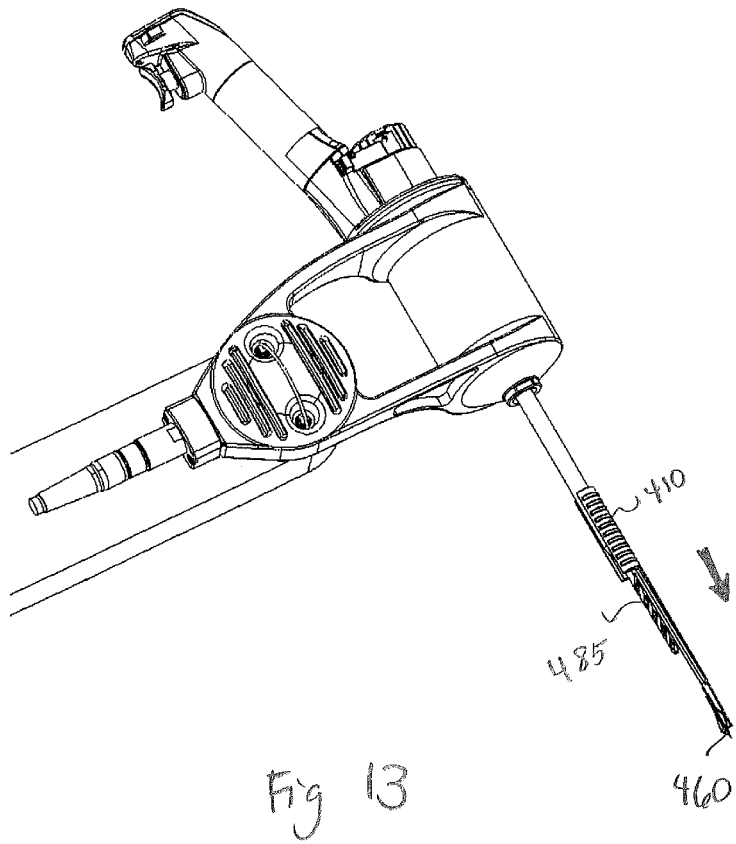

Incision tool 410 is designed to be used with an instrument and/or implant and robotic device 200, as shown in FIGS. 11-13. An instrument, shown as drill bit 485, can be inserted within and engaged with robotic end effector 210 such that the drill bit 485 extends distally from end effector 210 along a longitudinal axis of the drill bit. Incision tool 410 has a generally C-shaped cross-section to surround a portion of the instrument or drill bit 485 to releasably attach the incision tool 410 to the drill bit 485. Incision tool 410 hugs an outer diameter of the drill bit 485, and with a surgeon manually holding the incision tool 410 to the drill bit 485, the incision tool can be translated both distally and proximally along outer surface 487 of drill bit 485, as discussed in greater detail below, and can be positioned on the drill bit 485 in the desired orientation, e.g. vertical or horizontal, to allow the surgeon to choose the orientation of the incision based on the anatomy.

Incision tool 410 includes body 420 extending along a longitudinal axis. Body 420 includes a proximal portion 414 and a distal end, which includes attachment portion 428 substantially identical to second portion 128 of incision tool 110 which allows for a quick connection between the incision tool and a blade. Body 420 includes opposing exterior surface 422 and interior surface 426 each extending from the proximal portion to the distal portion. Interior surface 426 is generally concave along proximal portion 414 and first portion 424 of distal portion 418 to form valley 423, shown in FIG. 9. Interior surface 426 is generally smooth, while a portion of exterior surface includes raised bars 431 evenly spaced apart and extending in a direction transverse to the longitudinal axis of body 420. Raised bars 431 provide for a better grip on the device.

Figure 9:
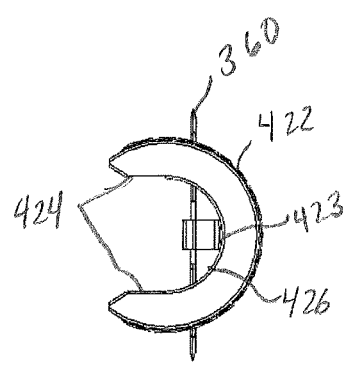

Proximal portion 414 of body 420 is generally C-shaped such that the widest diameter of the proximal portion, in a direction transverse to the longitudinal axis, is spaced apart from the terminal edges 415, as the terminal edges curl slightly back radially inwardly. FIG. 9 shows the arc shaped cross-section of proximal portion 414. Distal portion 418 may also be substantially C-shaped or it may alternatively be substantially U-shaped. Proximal portion 414 forms an opening or channel 413 such that drill bit 485 can occupy the passage when incision tool 410 is attached to the drill bit. The shape of the body allows for incision tool 410 to fit around drill bit 485 while still allowing the incision tool to translate relative to the instrument.

Figure 8:
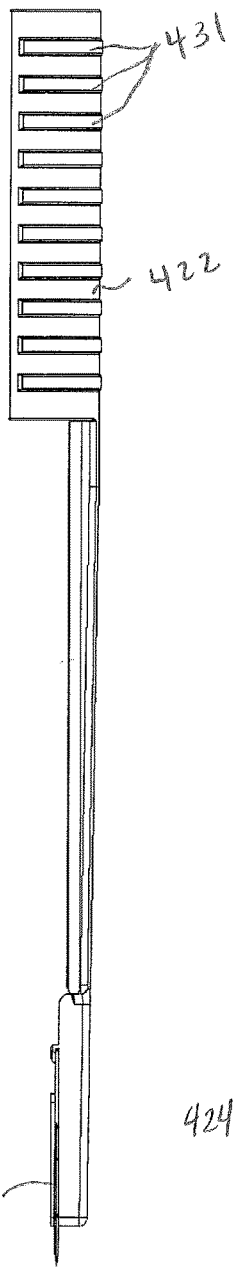

As shown in FIGS. 8 and 9, second portion 428 of distal portion 418 is not flush with valley 423 of body 420 extends further radially inward than the valley such that when blade 460 is attached to second portion 428 it too is positioned radially inward of valley 423 of body 420. As a result, a central axis of blade 460 is positioned substantially co-axial with the central longitudinal axis of drill bit 485 when outer surface 487 is in contact with interior surface 426, i.e. when incision tool 410 is assembled to drill bit 485.

Figure 10:
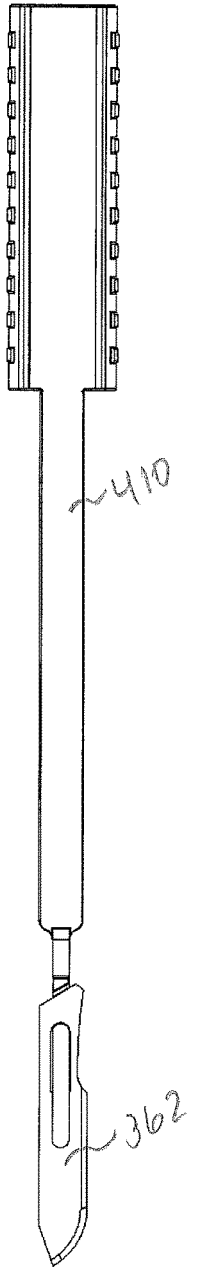
FIG. 10 is a side view of the incision tool of FIG. 6 in conjunction with an alternative blade in conjunction with another embodiment of the present disclosure.

The incision tools described herein, including incision tool 410, can be used in conjunction with a variety of blades, with quick attachment features provided at the distal ends of the incision tool. For example, FIG. 10 shows incision tool 410 with blade 362 attached to the distal end.

FIGS. 11-13 show incision system 410 in use with robotic device 200 and drill bit 485. Although shown with drill bit 485, other similar instruments may be used in conjunction with incision tool 410, such as a screwdriver and burr.

Drill bit 485 is loaded and secured within the robotic end effector 210. Incision tool 410 is placed onto the drill bit such that the drill bit is positioned within passageway 413. The surgeon can place incision tool 410 onto the drill bit in the desired orientation. A surgeon or other user manually slides incision tool 410 distally, shown in a comparison of FIGS. 12 and 13, to incise the tissue in a manner co-axial with the haptic control trajectory or predetermined static control trajectory set for the robotic device for which drill bit 485 is positioned along. The opening in tissue is incised in a single pass due to the front cutting edge and rear cutting edge of the blade, as described above. With drill bit 485 positioned against the opening and along the desired trajectory, incision tool 410 can be translated proximally and then detached from drill bit 485. After tool 410 is removed, robotic end effector 210 can be actuated to torque drill bit 485 to drill along the trajectory of the incision.

FIGS. 14-18 depict incision system 500 which includes incision tool 510 and blade 560. Blade 560 is similar to blade 160 described above, except that front cutting edge 564 has a convex shape rather than the concave shape of front cutting edge 164.

Incision tool 510 includes elongated body 520 including proximal portion 514 of body 520 which has a substantially C-shaped cross-section. Proximal portion 514 includes an attachment assembly for attaching the incision tool to another instrument for use during the surgery. In this embodiment, the attachment assembly includes hinged assembly 521, which includes leaf 529 secured to elongated body 520 by pin 523 received within at least one knuckle 524. Knuckle 524 curves radially outward from body 520 and leaf 529 curves radially back inward toward and extending over interior surface 526 of body 520 such that hinged assembly 521 of proximal portion 514 has a substantially C-shaped cross-section that drill bit 485 can be positioned within. Leaf 529 defines opening 537 for receiving pin 523 and the leaf is rotatable relative to pin 523. Proximal portion 514 further defines opening 513, shown in FIG. 16, for receiving a tool, such as drill bit 485. When drill bit 485 is positioned within opening 513 defined by proximal portion 514 of incision tool 510, leaf 529 is movable from a first open configuration in which the drill bit is not engaged with and/or limited in movement by incision tool and a second closed configuration in which leaf 529 is moved relatively further radially inward to impart a clamping force on drill bit 485 to engage the drill bit that is positioned within the incision tool 510. Leaf 529 is designed to allow a varying amount of force on drill bit 485 so that a surgeon has greater control on the positive connection between the drill bit and the incision tool which provides tactile feedback when the drill bit and the incision tool 510 are operatively coupled to one another.

Incision tool 510 further includes finger ring 527 disposed on exterior surface 522 and extending away from body 520. Finger ring 527 allows a surgeon to grasp the ring while also maintaining pressure on leaf 529 to control the connection between incision tool 510 and drill bit 485.

Figure 14:
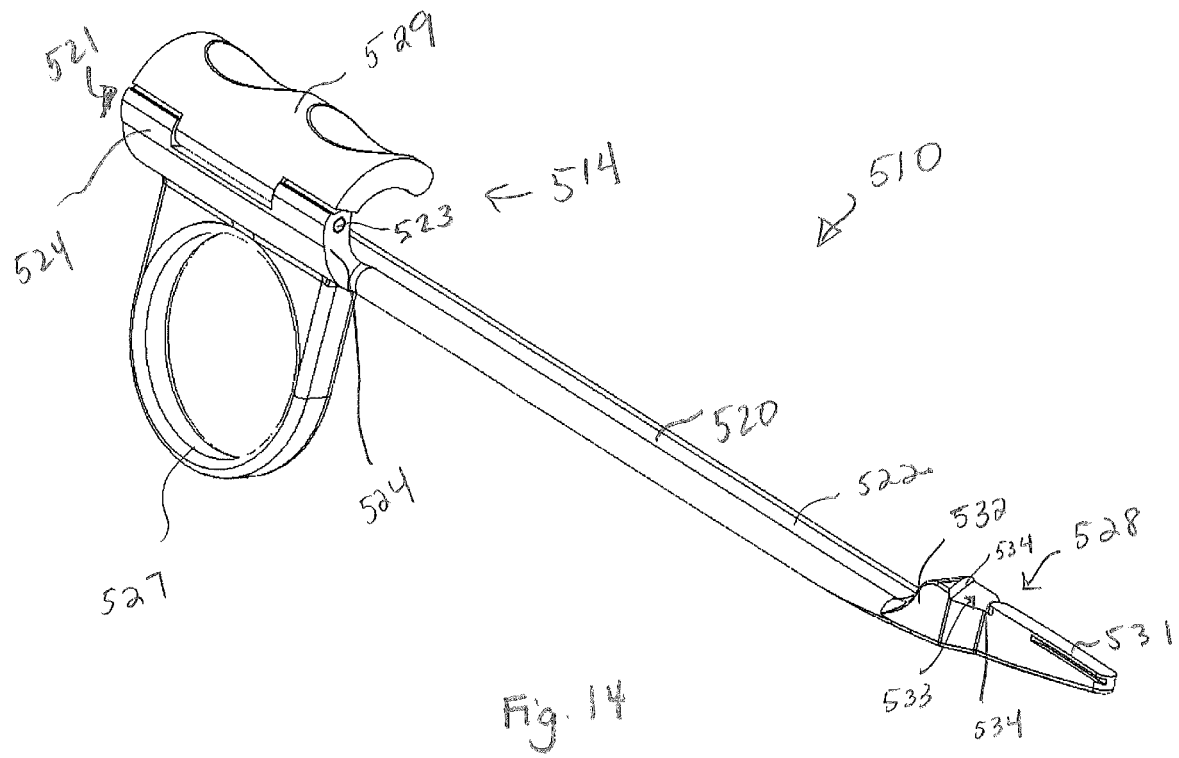
FIGS. 14-15 are a perspective side view and an exploded view, respectively, of an incision tool in accordance with an alternative embodiment of the present disclosure.
Figure 15:
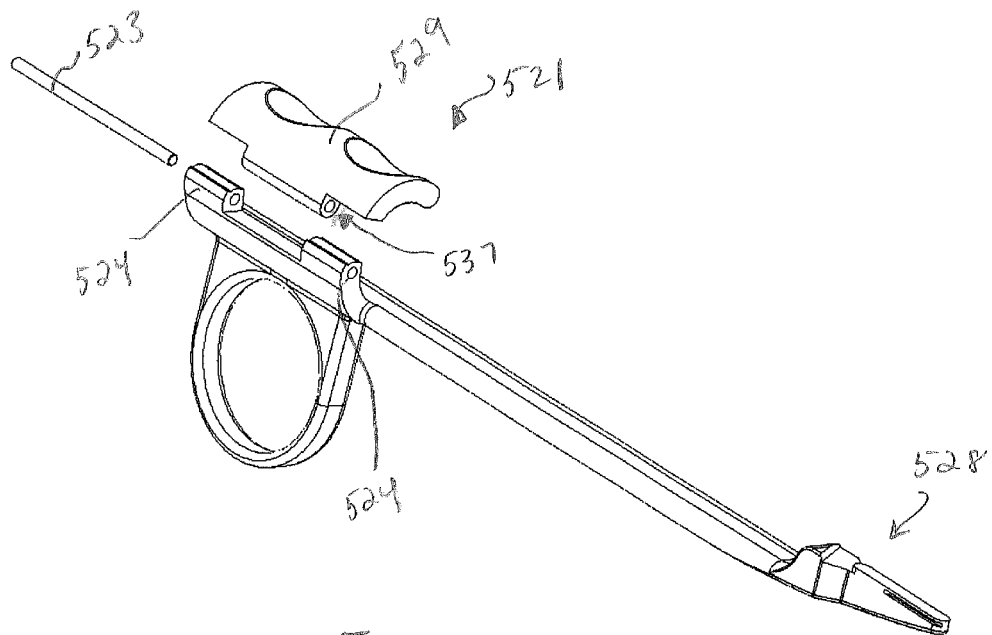
Figure 16:
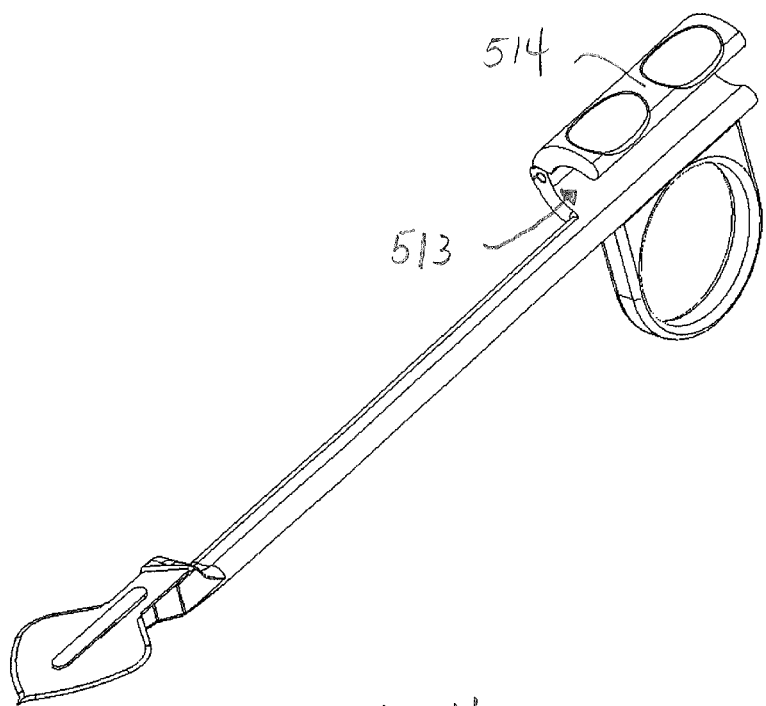
FIGS. 16-17 are a perspective side view and a perspective rear view, respectively, of an incision system including the incision tool of FIGS. 14 and 15 and a blade.
Figure 17:
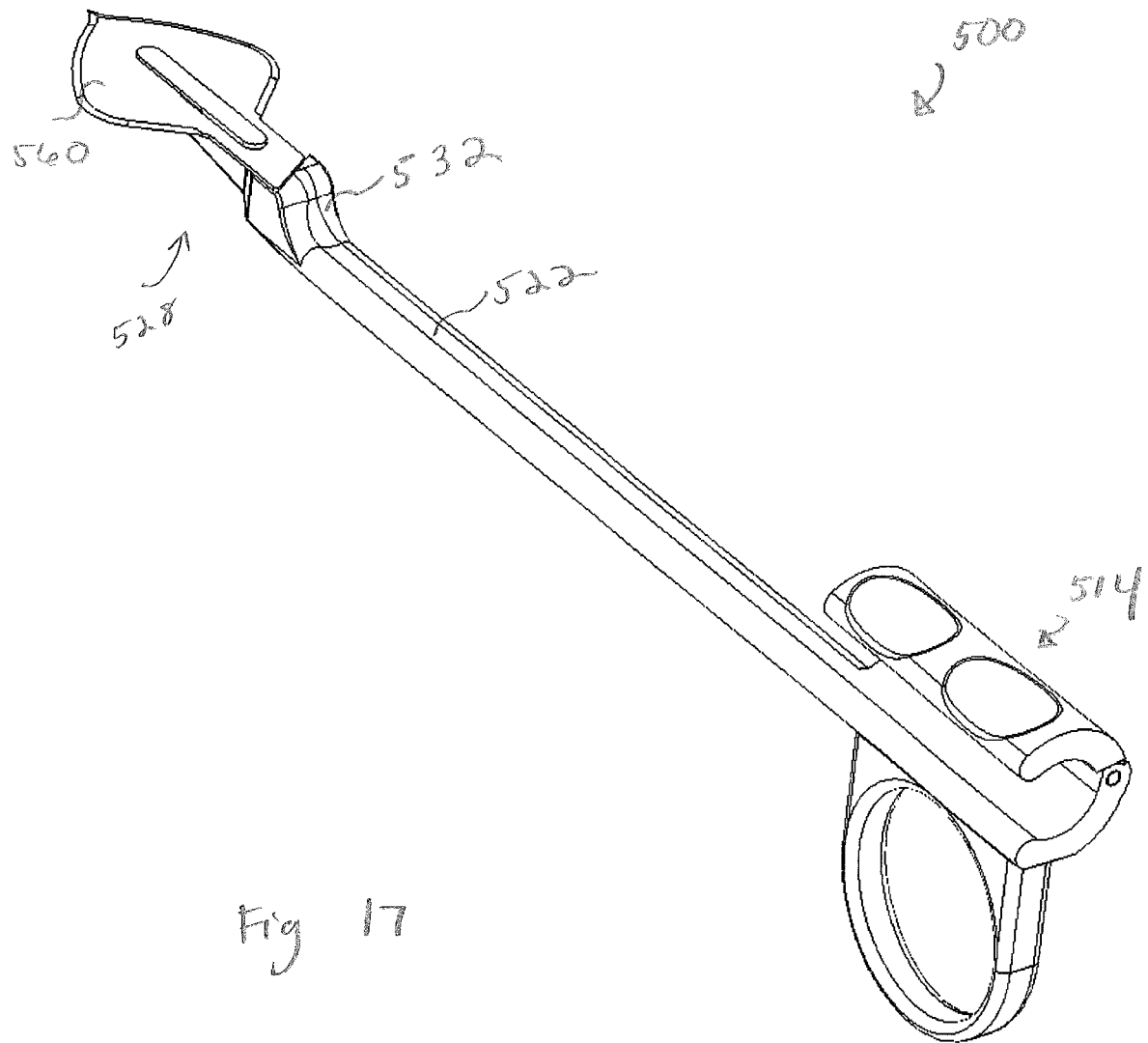

As shown in FIGS. 14 and 15, incision tool 510 includes attachment portion 528 at the distal end of the incision tool for attaching blade 560 to the incision tool. Attachment portion 528 is designed to easily and securely position blade 560 in engagement with incision tool 510. Attachment portion 528 includes raised portion 531 which is positionable within elongated aperture 561 of blade 560. Proximal to raised portion 531 is depressed portion or channel 533 extending across the width of attachment portion 528 and defined by opposing axially spaced apart inner surfaces 534. Interior surface 522 of elongated body 520 connects to attachment portion 528 at ski jump 532 which extends outwardly from interior surface 522 such that the attachment portion is raised relative to the interior surface 522 of the elongated body 520, as shown in FIG. 17.

Figure 18A:
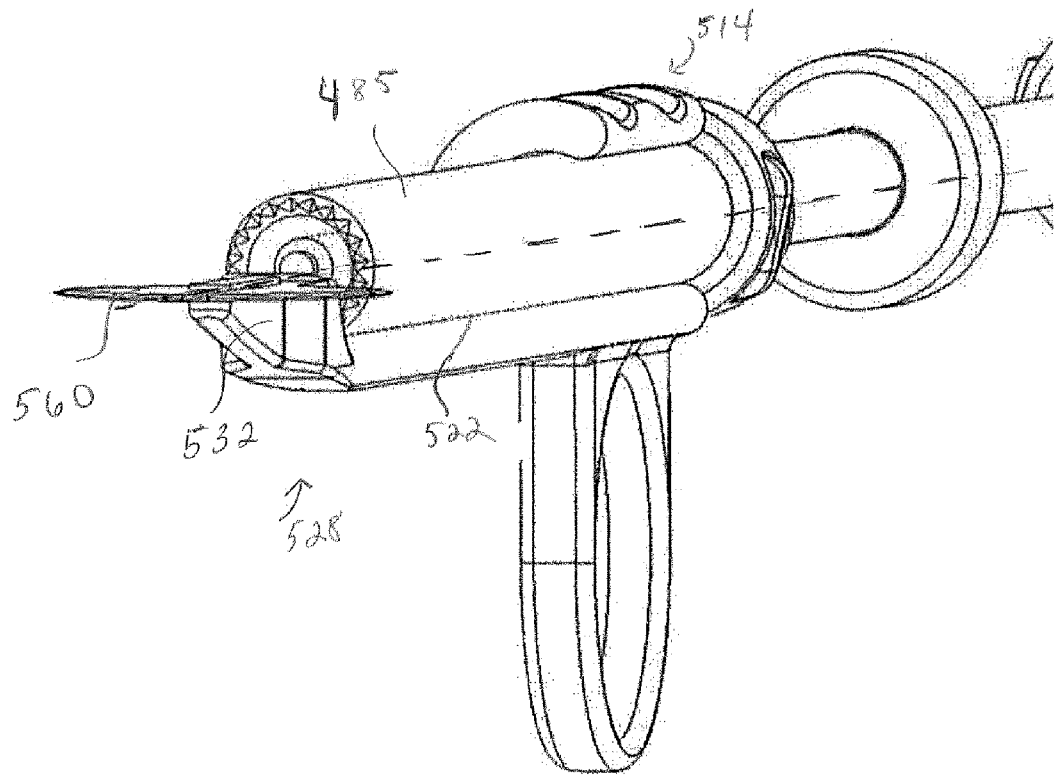
FIGS. 18A and 18B are perspective side views and FIG. 18C is a perspective bottom view of the incision tool of FIGS. 14 and 15 in conjunction with a cutting tool and a blade.
Figure 18B:
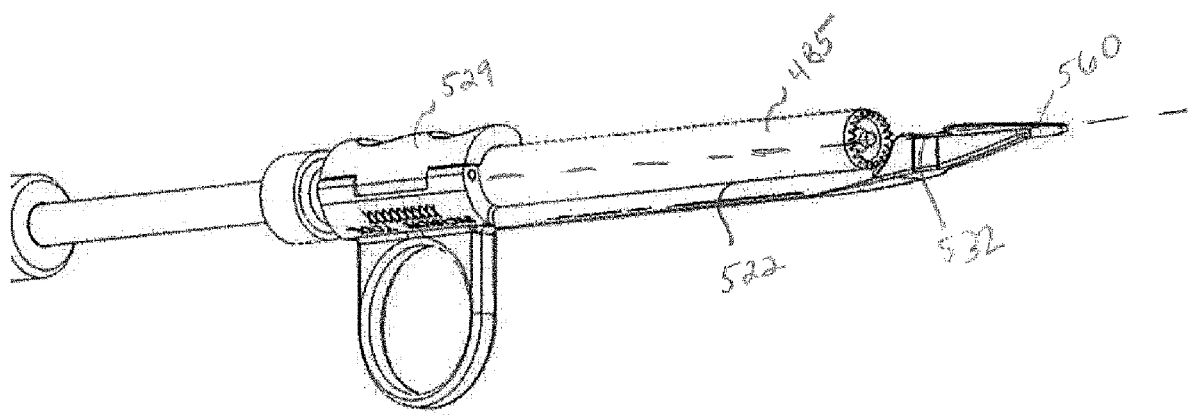
Figure 18C:
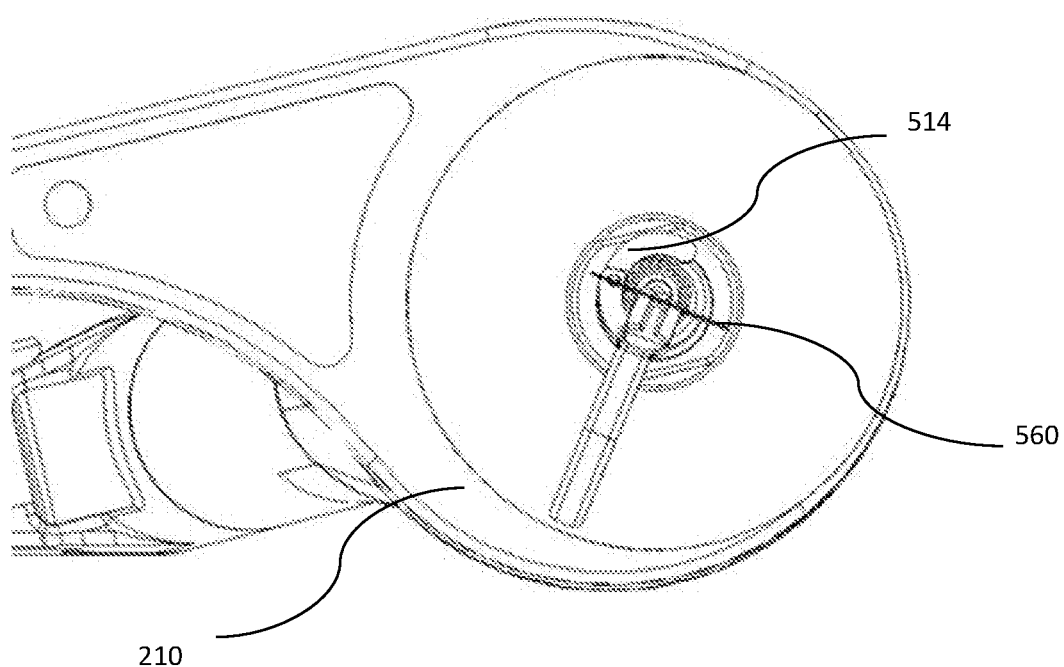
Figure 19:
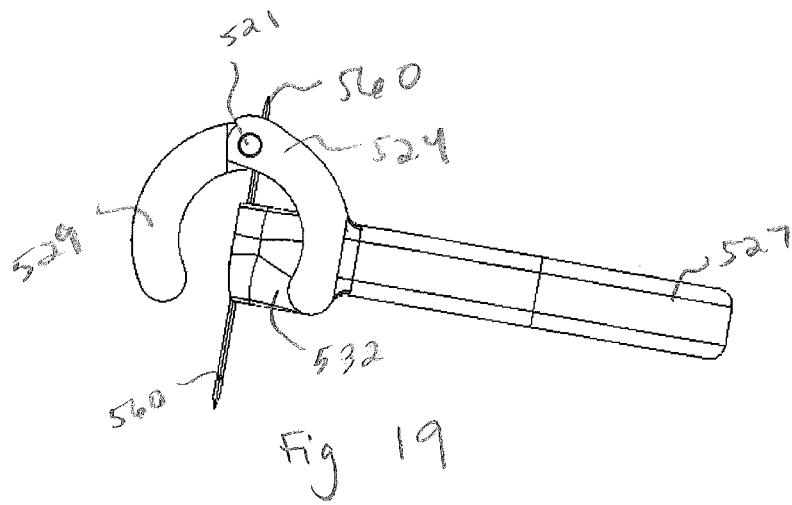
FIG. 19 is a top view of the incision tool of FIGS. 14 and 15 in conjunction with a blade.
Figures 20, 21:
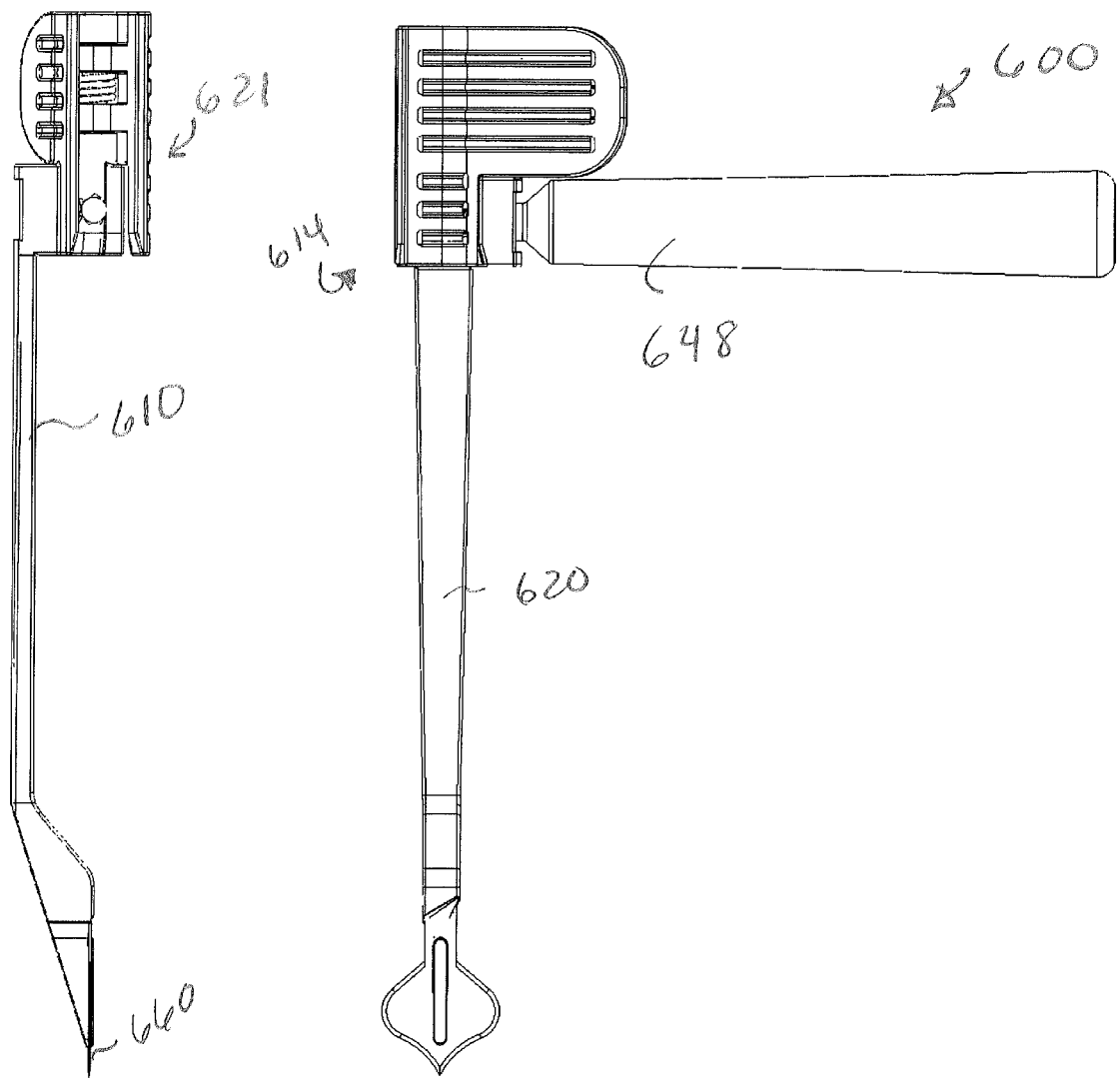
FIGS. 20-23 are a side view, a front view, a top view, and an exploded view, respectively, of an incision system including an alternative incision tool and a blade in accordance with another embodiment of the present disclosure.
Figure 22:
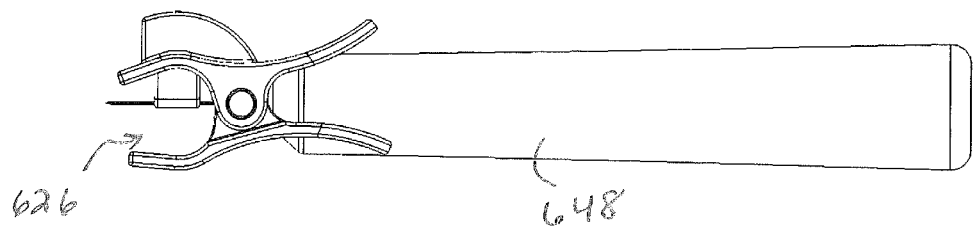

When blade 560 is secured to attachment portion 528, a central axis of the blade is co-axial with the central axis of the incision tool but is raised with respect to the plane on which the interior surface 522 extends, as shown in FIG. 19. Further, when system 500 is assembled with cutting tool 485 positioned within incision tool 510, blade 560 is co-axial with the central axis of the cutting tool, as shown in FIGS. 18A, 18B, and 18C.

In use, blade 560 is attached to incision tool 510. Drill bit 485 is loaded and secured within the robotic end effector 210. Incision tool 510 is positioned with hinged assembly 521 in the open configuration and positioned around drill bit 485. Leaf 529 of hinged assembly 521 is then moved radially inward into contact with drill bit 485 to engage the drill bit and provide an operative connection between the drill bit and the incision tool 510. Incision tool 510 is then translated distally along drill bit 485 and driven through a patient's soft tissue to make an incision. Incision tool 510 is translated proximally and blade 560 retracted out of the skin. Hinged assembly 521 is moved to the open configuration to disconnect the incision tool from drill bit 485. Drill bit 485 is then robotically powered to drill the opening that is in trajectory and/or rotational alignment with the incision for implanting the implant, e.g. screw. Although described with reference, to drill bit 485, the method can also be employed using a screwdriver, burr, or other similar tool.

Turning to FIGS. 20-26, incision system 600 includes incision tool 610, blade 660, and screwdriver 686 with screw 690 for implanting into a spine according to another embodiment of the present disclosure. Incision tool 610 has many similar features as incision tool 510, with similar features having the same reference numeral except in the 600 series. Incision tool 610 includes proximal portion 614 of body 620, which includes attachment assembly in the form of spring-loaded clip assembly 621 for loading the incision tool onto screwdriver 686.

Figure 23:
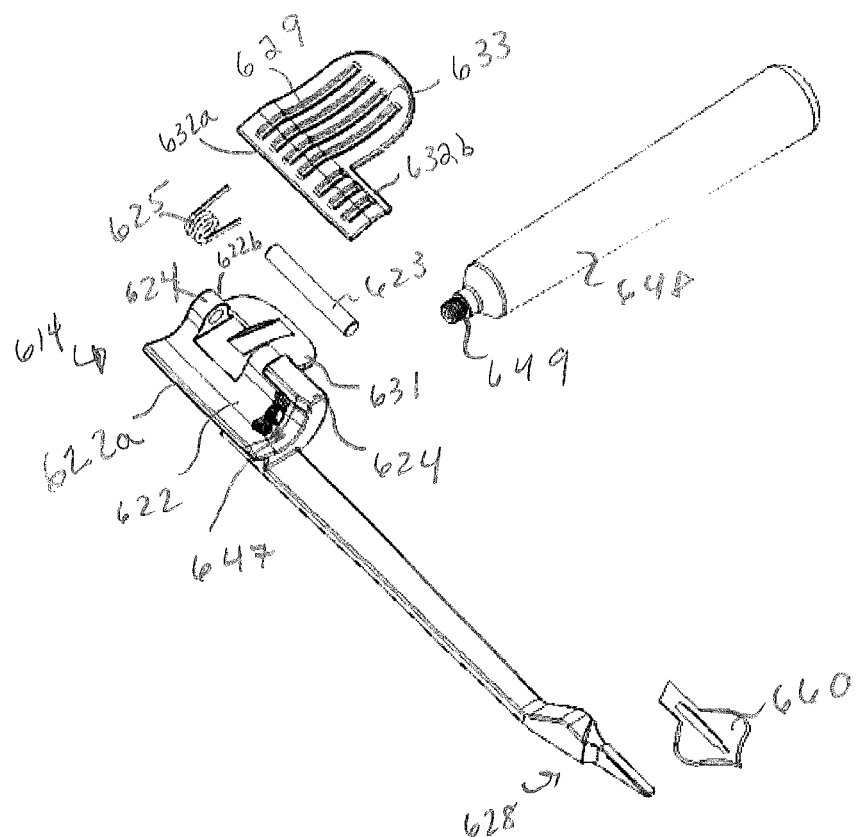

Clip assembly 621 includes base 622 defined by opposing first and second lateral edges 622a and 622b. As shown in FIG. 23, pin 623 is received within at least one knuckle 624 and at least partially surrounded by spring 625. Spring 625 is positioned within recess 627 of proximal portion 614, as shown in FIG. 23. Base 622 includes first flange 631 extending outwardly from second lateral edge 622b and which forms part of the clip member. Leaf 629 is rotatably connected to pin 623 and includes inner edge 632a and second flange 633 extending outwardly from outer edge 632b of leaf 629. Leaf 629 and base 622 define opening 626 therebetween for receiving screwdriver 686.

First and second flanges 631, 633 can be grasped by a surgeon to move the clip assembly 621, and in particular to move second flange 633, from a closed configuration in which inner edge 632a of leaf 629 is relatively closer to first lateral edge 622a of base 622 and an open configuration in which inner edge 632a of leaf 629 is relatively farther from first lateral edge 622a of base 622 which increases the size of opening 626. Further, during the transition from the closed configuration to the open configuration, second flange 633 moves in a direction toward first flange 631. Clip assembly 621 is biased such that at rest the assembly is in the closed configuration to hug an outer diameter of the screwdriver 686.

Handle 648 is attached to proximal portion 614 and has a substantially tubular shape to allow for easy gripping by a surgeon. In the illustrated embodiment, handle includes a threaded end 649 to screw into threaded opening 647 within base 622, which provides for detachment of the handle, if necessary.

Attachment portion 628 of incision tool 610 is substantially similar to attachment portion 528 of incision tool 510, the details of which are described in detail above.

Figure 24:
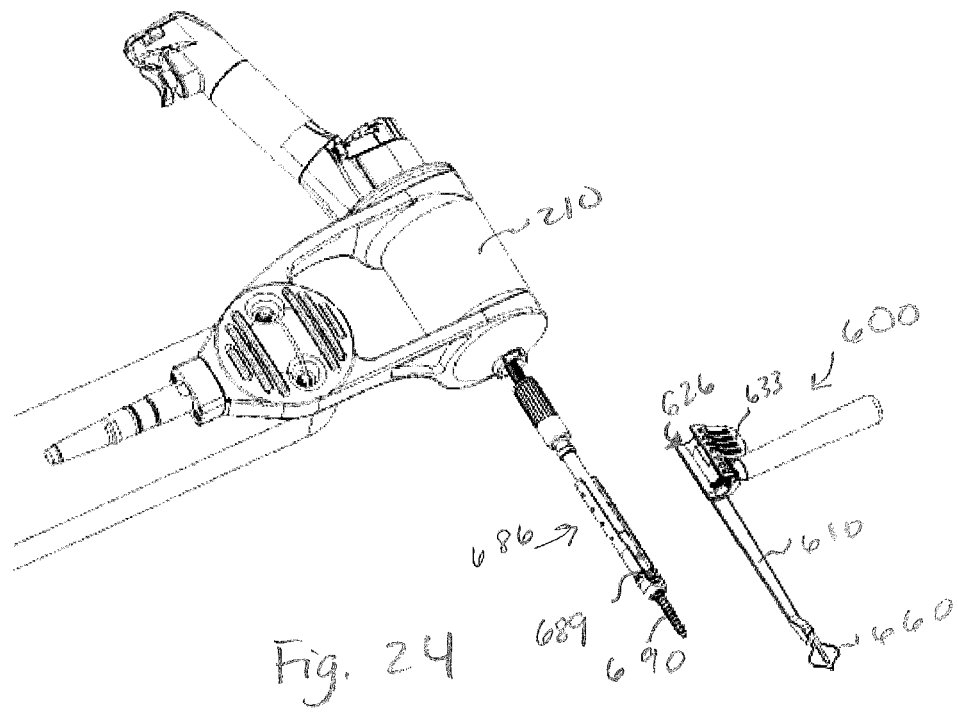
FIGS. 24-26 are perspective side views of the incision system of FIGS. 19-22 in conjunction with a screwdriver and an implant attached to the screwdriver and a robot.
Figure 25:
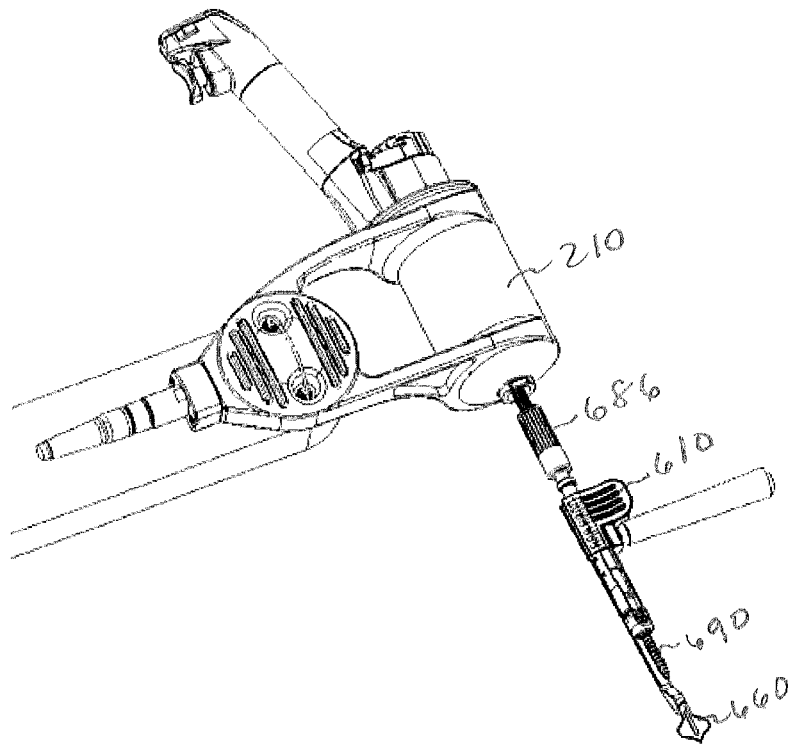

In use, screw 690 is inserted onto distal end 689 of screwdriver 686, and screwdriver 686 is loaded into robotic end effector 210, as shown in FIG. 24. Incision tool 610 (with blade 160 attached), and in particular clip assembly 621, is moved from the closed configuration to the open configuration to enlarge opening 626 so that screwdriver 686 fits within opening 626 and is by a surgeon pressing on first and second flanges 631, 633 to move second flange 633 to the open configuration. Second flange 633 is then released to move the clip assembly 621 to the closed configuration such that the screwdriver 686 is positioned within the incision tool 610, as shown in FIG. 25.

Figure 26:
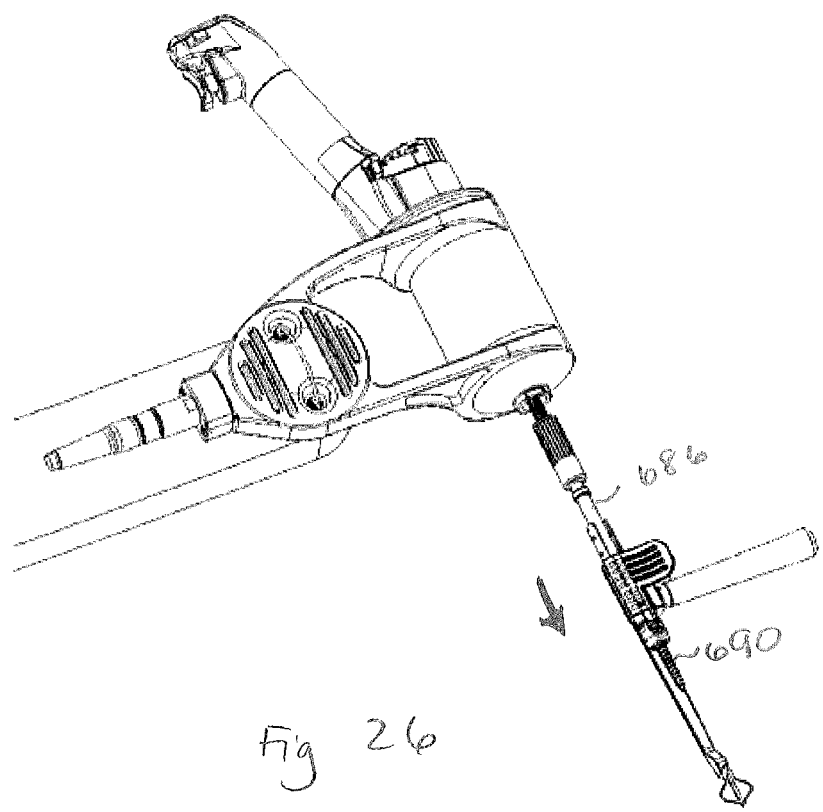

The surgeon, or other medical professional, can then hold handle 648 to translate incision tool 610 distally, shown in FIG. 26, to make an incision through the patient's tissue and subsequently retracted in a proximal direction along screwdriver 686 to create an incision that is formed in a single pass. The incision created within the patient is co-axial with the trajectory of the longitudinal axis that the screwdriver 686 and screw 690 extend along. Clip assembly 621 is transitioned into the open configuration to detach the incision tool 610 from the screwdriver 686. The screwdriver is then actuated by the robotic end effector 210 to drive screw 690 into bone along the trajectory of the incision.

FIGS. 27-32 show enlarged views of various embodiments of single pass blades designed for easy attachment to any one of the incision tools described above. Such embodiments are similar to blade 160, shown in FIG. 27 and described in detail above with reference FIGS. 1 and 2; only the differences of each embodiment will be described below.

Figure 28:
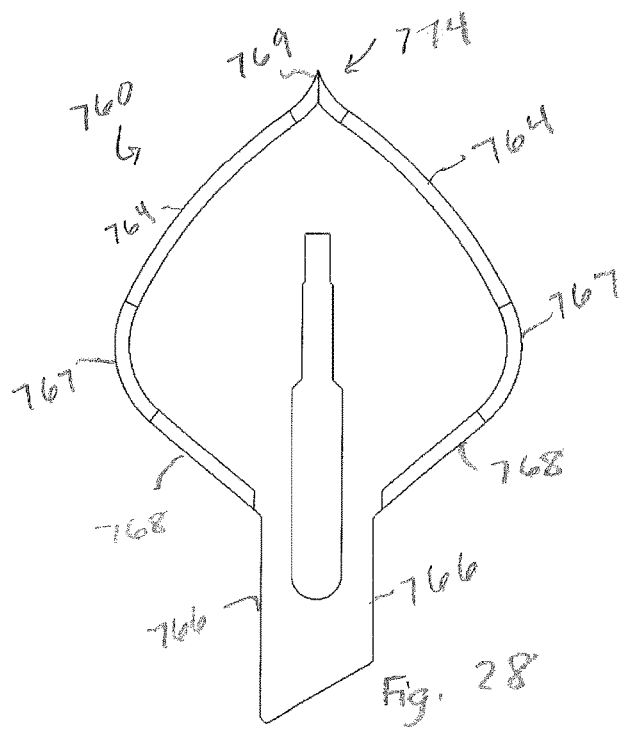
Figure 29:
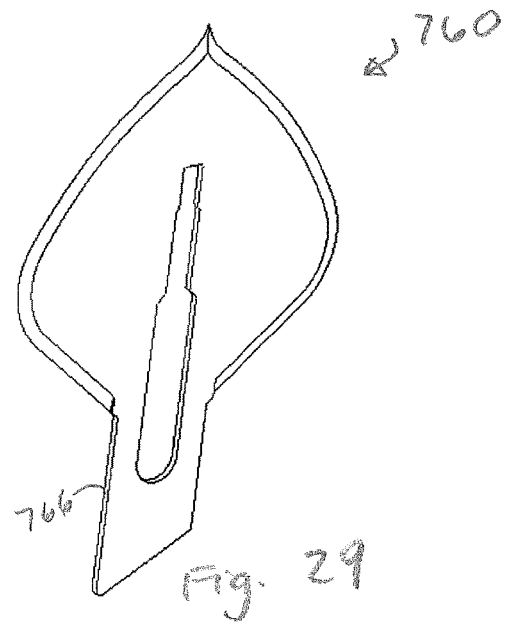
FIG. 29 is a front view of an alternative embodiment of a blade in accordance with another embodiment of the present disclosure.

FIGS. 28 and 29 show blade 760 which is substantially spade shaped. Blade 760 includes distal end 774 and proximal end 778. Proximal end 778 includes terminating edge 765 connecting two lateral sides 766. Blade 760 includes front cutting edge 764, e.g. when moving in the distal direction and/or into the tissue, and rear cutting edge 768, e.g. when moving in the proximal direction and/or retracting from the bone. Rear cutting edge 768 extend from sides 766 and flare outward to hips 767 that define the maximum width of the blade, defined in a direction transverse to the longitudinal axis of the blade. Hips 767 extend inward distally to define front cutting edge 764 and extend to a concave sharp distal tip 769. In this example, front cutting edge 764 is convex and rear cutting edge 768 is convex or linear. Blade 760 includes similar attachment features to attach the blade to the incision tools described herein.

Figure 30:
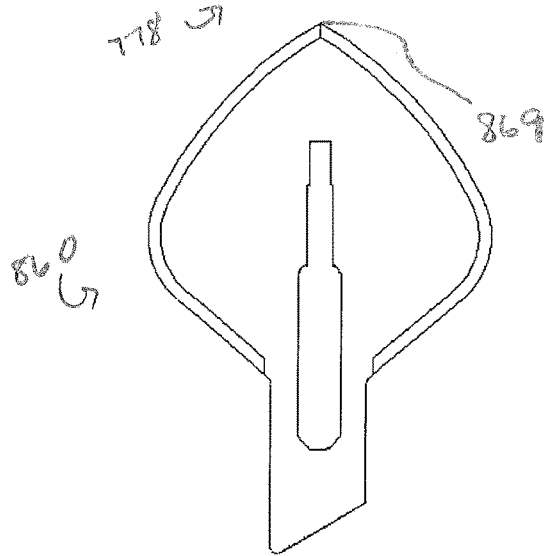
FIG. 30 is a front view of yet another alternative embodiment of a blade in accordance with another embodiment of the present disclosure.
Figure 31:
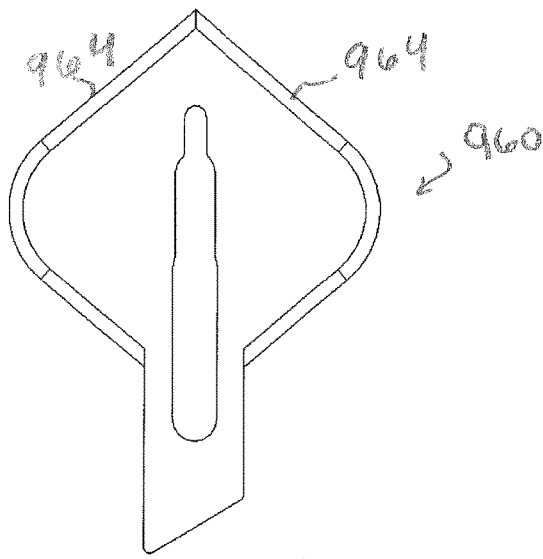
FIG. 31 is a front view of yet another alternative embodiment of a blade in accordance with another embodiment of the present disclosure.
Figure 32:
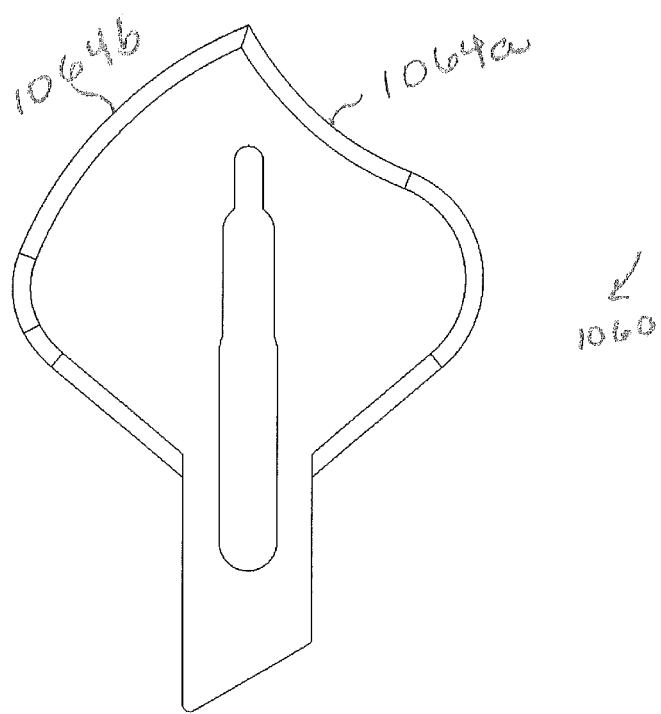
FIG. 32 is a front view of yet another alternative embodiment of a blade in accordance with another embodiment of the present disclosure.

FIG. 30 shows blade 860 which is substantially similar to blade 760, except that distal tip 869 is relatively more rounded than distal tip 769 of blade 760. FIG. 31 shows blade 960 which differs from blades 160 and 760 in that front cutting edge 964 is substantially linear, which may contribute to lower cutting forces and smoother insertion. FIG. 32 shows blade 1060 which is asymmetrical about the longitudinal axis of the blade such that first portion 1064a of front cutting edge 1064 is concave and second portion 1064b of front cutting edge 1064 is convex. Second portion 1064b may provide a smoother cut while first portion 1064a provides a sharp tip.

FIGS. 33-37 show incision system 1600 according to another embodiment of the present disclosure. Incision system 1600 includes incision tool 1610 configured to be received within end effector guide tube 1670 attached to a robotic arm 1660 of a robotic system and engageable with the end effector guide tube 1670 to translate the incision tool to form an incision in the patient. System 1600 is designed to facilitate the trajectory alignment of various tools during the surgery, including for example, the incision tool, the drill, and the screwdriver. Further, system 1600 allows for rotational alignment of the various tools so that the orientation of the incision can be controlled based on the needs for the surgery. Each tool is designed to be positioned within the end effector guide tube 1670, which enables the trajectories or each tool to be the same relative to one another. For example, with incision tool 1610 within the guide tube, the incision tool is able to be angulated to control the rotational orientation of the blade during incision.

Figure 33:
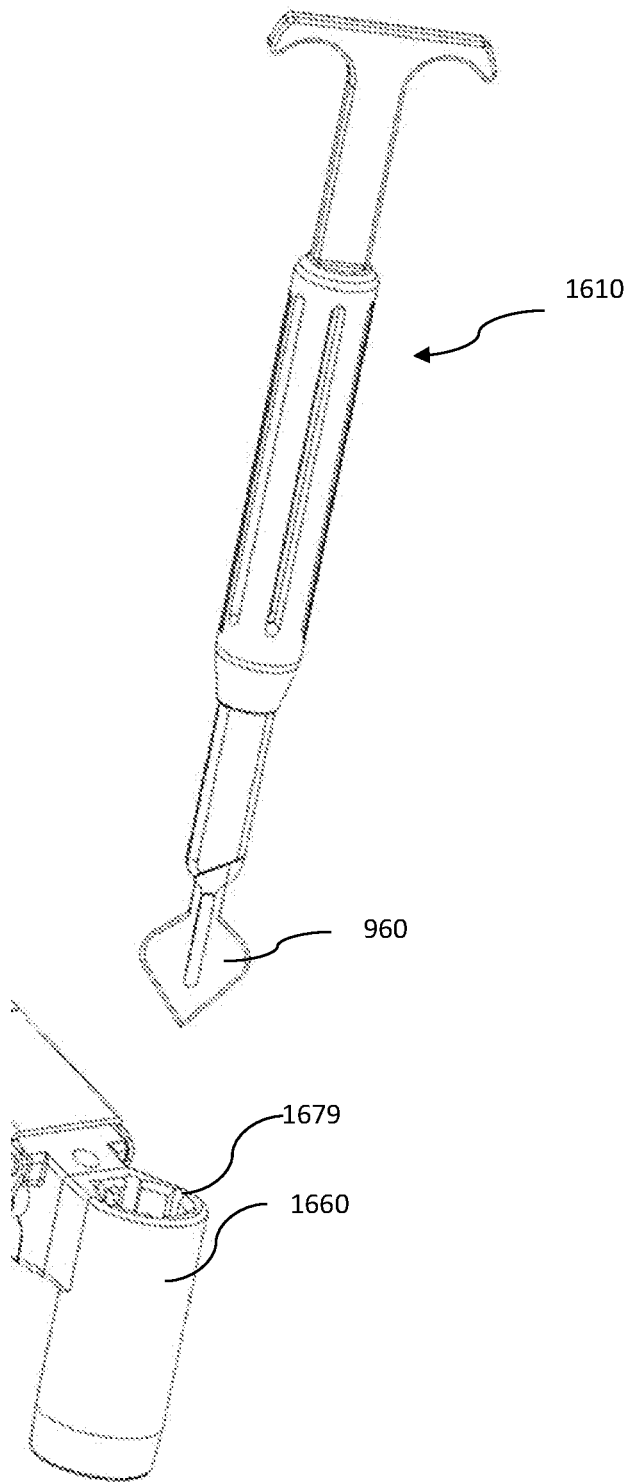
FIG. 33 is a perspective front view of an incision system including an alternative incision tool, a blade and a guide tube in accordance with another embodiment of the present disclosure.
Figure 34:
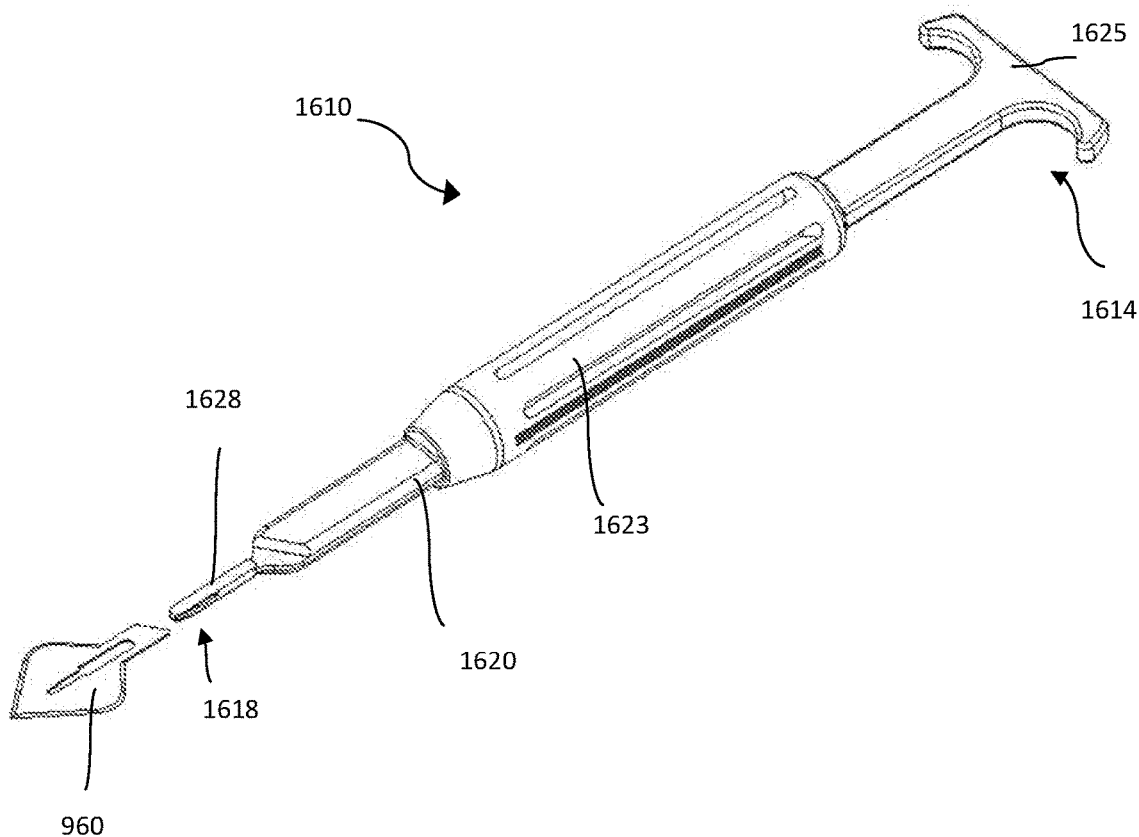
FIG. 34 is a perspective side view of the incision tool and blade of FIG. 33, with the blade detached from the incision tool.
Figure 35:
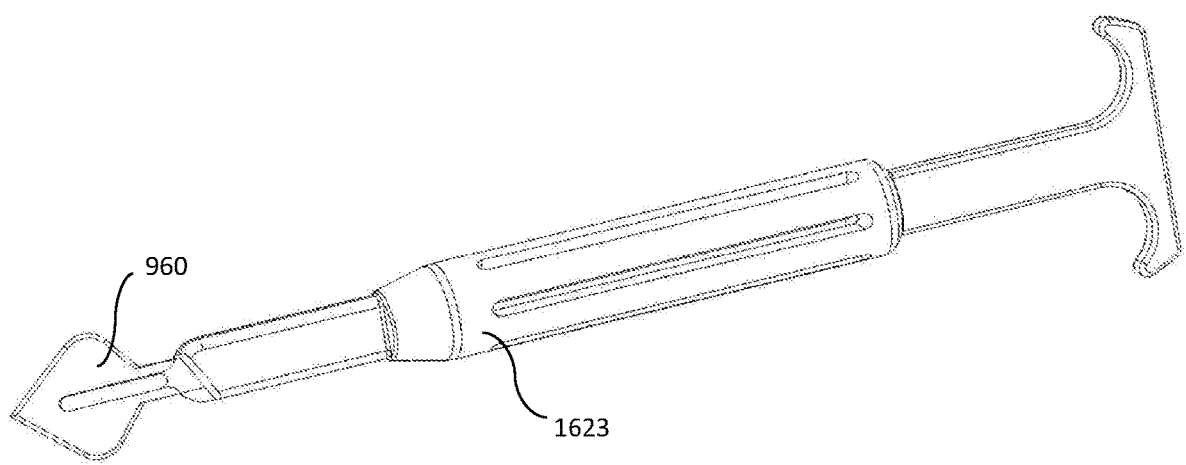
FIG. 35 is a perspective front view of the incision tool and blade of FIG. 33 with the blade attached to the incision tool.

As shown in FIG. 33, incision tool 1610 is sized and shaped to be positioned within end effector guide tube 1670. Incision tool 1610 includes body 1620 extending between proximal end 1614 and distal end 1618. At proximal end 1614, body 1620 includes handle 1625 for a user to grip and control the tool. At distal end 1618, body 1620 includes attachment portion 1628 substantially similar to second portion 128 of incision tool 110, and allows for a quick connection between the incision tool 1610 and a blade. In the illustrated embodiment, incision tool is shown in conjunction with blade 960.

Body 1620 includes central portion 1623 between proximal end 1614 and distal end 1618 which is sized and configured to fit within guide tube 1670 of the robotic system such that the central portion is able to translate axially and rotate freely within guide tube 1670. This enables the surgeon to be able to control the angulation of the incision tool 1610 and blade 960 for the angle of insertion.

Guide tube 1670 includes longitudinal slots 1679, shown in FIG. 33, which allow for clearance for blade 960 as the blade passes through the guide tube 1670. After the blade is passed through the distal end of the guide tube, the system allows for control of the trajectory and angulation/rotation of the incision tool including blade 960. Incision tool 1610 may include a laser marking to indicate when the blade is in a certain position.

Figure 36:
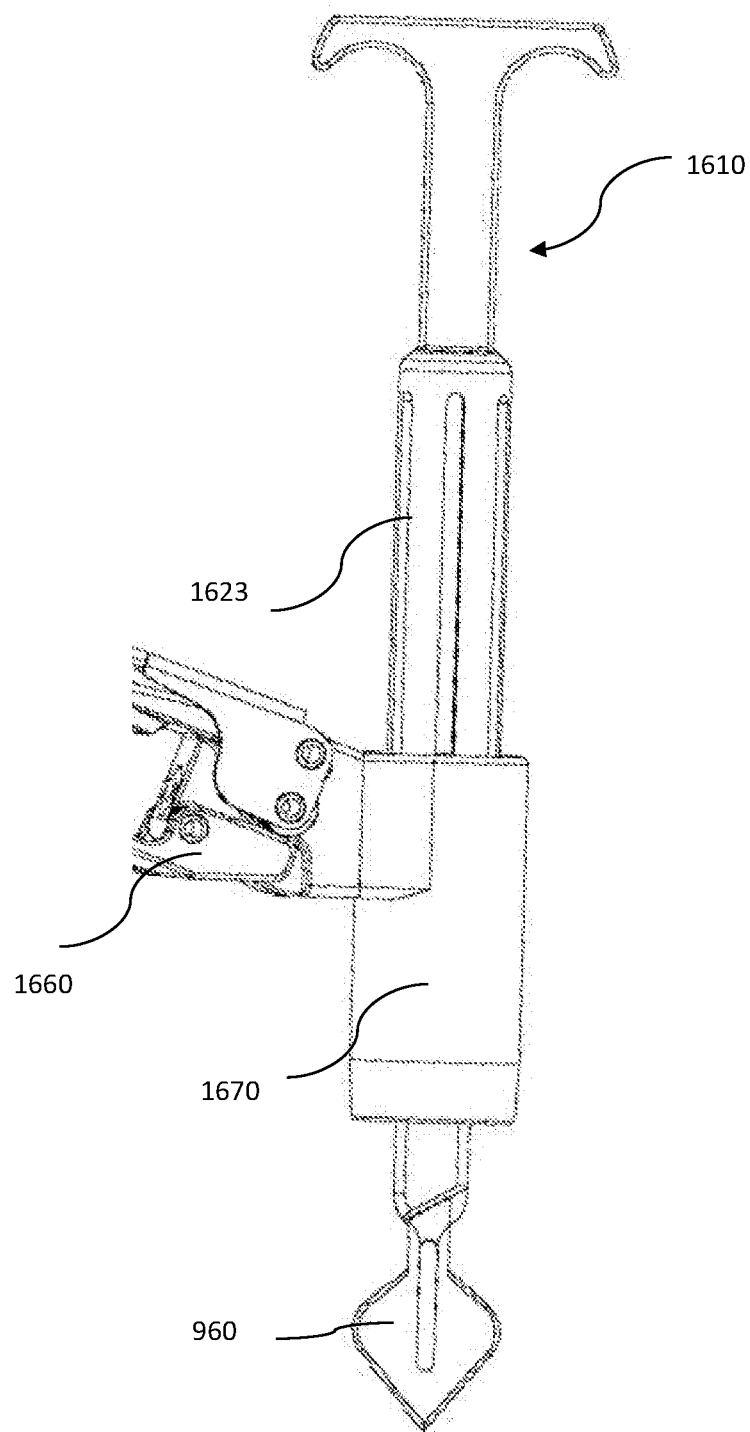
FIGS. 36 and 37 is a perspective front view and a cross-sectional view, respectively of the incision tool in conjunction with a guide tube of a robotic system.
Figure 37:
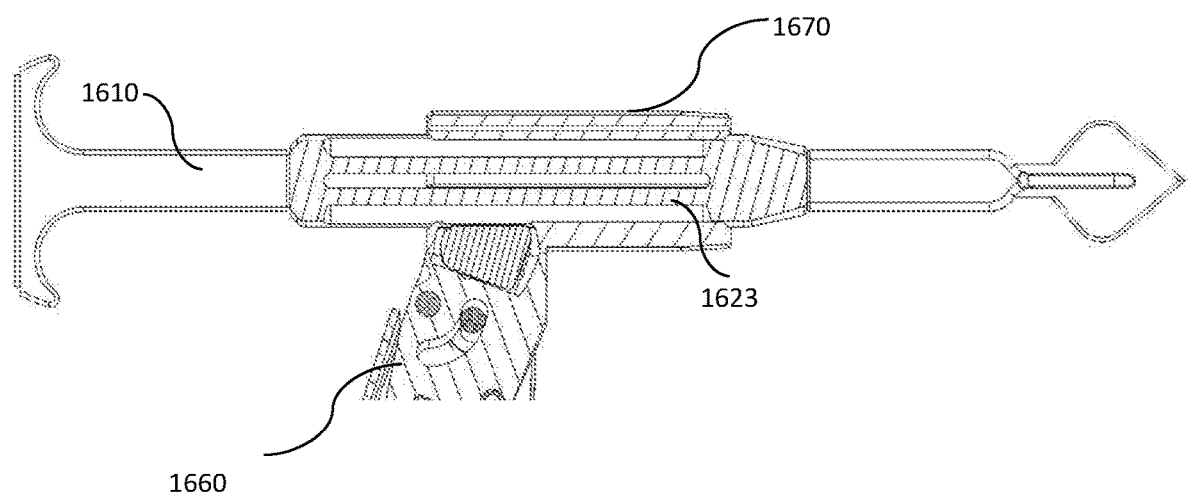

As shown in FIGS. 36 and 37, with blade 960 attached at the distal end 1618, incision tool 1610 is positioned within end effector guide tube 1670 of the robotic system. By allowing angulation and rotation of the incision tool 1610 within guide tube 1670, the surgeon is able to control the orientation of the blade upon insertion. The incision tool makes an incision in the soft tissue via blade 960 along the desired trajectory. After the incision is made, incision tool 1610 is removed by pulling it proximally, and the subsequent steps of surgery are performed with the respective tools travelling through the guide tube along the same desired trajectory for accurate and efficient placement of the implant, e.g. tapping, drilling, and driving the implant.

In some embodiments, the system may include a locking mechanism to allow the surgeon to fix the trajectory and/or rotational orientation of the incision tool within the guide tube.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tool for creating an incision at a surgical site comprising:
   a body for use with a robotic end effector, the body including a blade attachment portion at a distal portion of the body, and a handle arranged for a user to grip at a proximal portion of the body; and
   a blade detachably secured to the body, the blade having a longitudinal axis extending along a direction between a proximal end and a distal end, the blade having a cutting edge symmetric about the longitudinal axis and defining: a first portion including a pair of linear rear cutting edges extending outwardly from or adjacent to the proximal end, a second portion including a pair of linear front cutting edges extending inwardly to a sharp distal tip, and a pair of curved hips transitioning between the linear rear cutting edges and the linear front cutting edges and defining a maximum width of the blade;
   wherein the proximal portion of the body forms an attachment assembly, the attachment assembly is a clip assembly including a spring-loaded leaf; and
   wherein the proximal portion of the body has a C-shaped cross-section.

2. The tool of claim 1, wherein the blade attachment portion of the body includes an elongated projection and the blade includes a corresponding elongated recess for receiving the elongated projection of the body to attach the blade to the body.

3. The tool of claim 1, wherein the clip assembly includes a base having a first flange and the leaf has a second flange.

4. The tool of claim 3, wherein an opening is defined between the base and the leaf, wherein the clip assembly is moveable between a closed configuration and an open configuration and the opening is larger in the open configuration than in the closed configuration.

5. The tool of claim 4, wherein the tool is a first tool and in the closed configuration, a second tool is positionable within the first tool and the first tool is operatively secured to the end effector.

6. The tool of claim 5, wherein the first tool is an incision tool and the second tool is a driver.

7. A system comprising:
   the tool of claim 1; and
   an end effector guide tube attachable to a robotic arm, wherein the tool is configured to be positioned within the guide tube.

8. The tool of claim 1, wherein the tool is an incision tool and is configured to receive a second tool, wherein the proximal portion of the incision tool forms an opening configured to selectively receive the second tool.

9. The tool of claim 8, wherein the proximal portion of the incision tool is configured to allow translational movement of the incision tool relative to the second tool, while the second tool is disposed through at least the proximal portion of the incision tool.

10. The tool of claim 1, wherein the distal portion is substantially c-shaped.

11. The tool of claim 10, wherein the proximal portion and the distal portion are each configured with an opening to selectively receive a second tool.

12. The tool of claim 1, wherein the blade attachment portion includes quick attachment features.

13. The tool of claim 1, wherein the tool is configured to engage a portion of the end effector with the proximal portion of the body.

14. The tool of claim 13, wherein the end effector includes a drill bit and the proximal portion of the body receives at least a portion of the drill bit.

15. A method of incising an opening in a subject comprising:
   attaching a blade to an attachment assembly of a body of an incision tool, the blade having a symmetric cutting edge defining: a first portion including a pair of linear rear cutting edges extending outwardly from or adjacent to a proximal end, a second portion including a pair of linear front cutting edges extending inwardly to a sharp distal tip, and a pair of curved hips transitioning between the linear rear cutting edges and the linear front cutting edges and defining a maximum width of the blade;
   positioning a first portion of the incision tool within a robotic end effector; and
   advancing the incision tool distally so that the blade attached to the incision tool cuts into tissue along a first trajectory;
   wherein the proximal portion of the body forms an attachment assembly, the attachment assembly is a clip assembly including a spring-loaded leaf; and
   wherein the incision tool includes a handle arranged for a user to grip at a proximal portion of the body and wherein the proximal portion of the body has a C-shaped cross-section.

16. The method of claim 15, further comprising the step of removing the incision tool from the robotic end effector.

17. The method of claim 15, further comprising the steps of positioning a cutting tool within the robotic end effector and advancing the cutting tool into bone along the first trajectory.

18. A tool for creating an incision at a surgical site comprising:
   a body for use with a robotic end effector, the body including a blade attachment portion at a distal portion of the body, and a handle arranged for a user to grip at a proximal portion of the body; and
   a blade detachably secured to the body, the blade having a longitudinal axis extending along a direction between a proximal end and a distal end, the blade having a cutting edge symmetric about the longitudinal axis and defining: a first portion including a pair of linear rear cutting edges extending outwardly from or adjacent to the proximal end, a second portion including a pair of linear front cutting edges extending inwardly to a sharp distal tip, and a pair of curved hips transitioning between the linear rear cutting edges and the linear front cutting edges and defining a maximum width of the blade;

wherein the proximal portion of the body forms an attachment assembly, wherein the attachment assembly is a hinged assembly including a hinged leaf; and wherein the proximal portion of the body has a C-shaped cross-section.

19. The tool of claim 18, wherein the tool is an incision tool and is configured to receive a second tool, wherein the proximal portion of the incision tool forms an opening configured to selectively receive the second tool.

\* \* \* \* \*